(12) United States Patent
Pedersen et al.

(10) Patent No.: US 8,604,225 B2
(45) Date of Patent: Dec. 10, 2013

(54) METHOD OF PRODUCING HYDROXYMETHYL-FURFURAL

(75) Inventors: Sven Pedersen, Gentofte (DK); Troels B. Christensen, Birkeroed (DK); Astrid Boisen, Soeborg (DK); Vibeke W. Jurgensen, Gentofte (DK); Thomas S. Hansen, Soeborg (DK); Soeren Kegnaes, Copenhagen (DK); Anders Riisager, Taastrup (DK); John M. Woodley, Copenhagen (DK); Jacob S. Jensen, Herlev (DK); Wenjing Fu, Copenhagen (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 13/638,684

(22) PCT Filed: Apr. 7, 2011

(86) PCT No.: PCT/EP2011/055416
§ 371 (c)(1),
(2), (4) Date: Oct. 1, 2012

(87) PCT Pub. No.: WO2011/124639
PCT Pub. Date: Oct. 13, 2011

(65) Prior Publication Data
US 2013/0029383 A1     Jan. 31, 2013

Related U.S. Application Data

(60) Provisional application No. 61/324,867, filed on Apr. 16, 2010, provisional application No. 61/362,756, filed on Jul. 9, 2010.

(30) Foreign Application Priority Data

Apr. 7, 2010   (EP) .................................. 10159243
Apr. 16, 2010  (EP) .................................. 10160131
Jul. 2, 2012   (EP) .................................. 10168267

(51) Int. Cl.
*C07D 307/02* (2006.01)

(52) U.S. Cl.
USPC ........... 549/503; 568/300; 568/420; 568/446; 568/700; 568/838

(58) Field of Classification Search
None
See application file for complete search history.

(56) References Cited

U.S. PATENT DOCUMENTS

| 4,977,283 | A | 12/1990 | Leupold et al. |
| 7,317,116 | B2 | 1/2008 | Sanborn |
| 7,411,078 | B2 | 8/2008 | Miura et al. |
| 7,572,925 | B2 * | 8/2009 | Dumesic et al. ............. 549/488 |
| 2008/0033188 | A1 | 2/2008 | Dumesic et al. |
| 2008/0103318 | A1 | 5/2008 | Lilga et al. |
| 2009/0030215 | A1 | 1/2009 | Dignan et al. |

FOREIGN PATENT DOCUMENTS

| WO | 2007/146636 A1 | 12/2007 |
| WO | 2008/019219 A1 | 2/2008 |

OTHER PUBLICATIONS

Boisen et al., Chemical Engineering Research and Design, vol. 87, No. 9, pp. 1318-1327 (2009).
Huang et al., Chem. Commun., vol. 46, pp. 1115-1117 (2010).
Moreau et al., Journal of Molecular Catalysis A: Chemical, vol. 253, Nos. 1-2, pp. 165-169 (2006).
Qi et al., Catalysis Communications, vol. 10, pp. 1771-1775 (2009).
Roman-Leskhov et al., Top. Catal., vol. 52, pp. 297-303 (2009).
Roman-Leskhov et al., Nature, vol. 447, No. 7147, pp. 982-986 (2007).
Zhao et al., Science, vol. 316, pp. 1597-1600 (2007).

* cited by examiner

*Primary Examiner* — Sudhakar Katakam
(74) *Attorney, Agent, or Firm* — Elias Lambiris

(57) ABSTRACT

The present invention relates to a method of producing 5-hydroxymethylfurfural by dehydration of fructose and/or glucose and/or mannose.

10 Claims, 14 Drawing Sheets

METHOD OF PRODUCING HYDROXYMETHYL-FURFURAL

CROSS-REFERENCE TO RELATED APPLICATIONS

This application is a 35 U.S.C. 371 national application of PCT/EP2011055416 filed Apr. 7, 2011, which claims priority or the benefit under 35 U.S.C. 119 of European application nos. 10159243.4, 10160131.8, and 10168267.2 filed Apr. 7, 2010, Apr. 16, 2010, and Jul. 2, 2010, respectively and U.S. provisional application Nos. 61/324,867 and 61/362,756 filed Apr. 16, 2010 and Jul. 9, 2010, respectively, the contents of which are fully incorporated herein by reference.

FIELD OF THE INVENTION

The present invention relates to a method of producing 5-hydroxymethylfurfural.

BACKGROUND OF THE INVENTION

Many chemical compounds needed for various industries have for many years been derived from the petrochemical industry. However, due to increases in the price of crude oil and a general awareness of replacing petrochemicals with renewable resources there has been and still is a wish to base the production of chemical compounds on renewable resources.

5-hydroxymethylfurfural (HMF) is an example of such a compound because it is derived from dehydration of sugars making it derivable from renewable biomass resources. HMF can for example be converted to 2,5-dimethylfuran by hydrogenolysis of C—O bonds over a copper-ruthenium (CuRu) catalyst (Roman-Leshkov Y et al., Nature, 2007, 447 (7147), 982-U5), which is a liquid biofuel or to 2,5-furandicarboxylic acid by oxidation (Boisen A et al., Chemical Engineering Research and Design, 2009, 87(9), 1318-1327). The latter compound, 2,5-furandicarboxylic acid, can be used as a replacement of terephthalic acid in the production of polyesters such as polyethyleneterephthalate (PET) and polybutyleneterephthalate (PBT).

US 2008/0033188 discloses a catalytic process for converting sugars to furan derivatives, e.g. 5-hydroxymethylfurfural, using a biphasic reactor containing a reactive aqueous phase and an organic extracting phase.

Román-Leshkov Y and Dumesic J A, 2009, Top Catal, 52; 297-303 discloses similar subject-matter as US 2008/0033188.

US 2009/0030215 discloses a method of producing HMF by mixing or agitating an aqueous solution of fructose and inorganic acid catalyst with a water immiscible organic solvent to form an emulsion of the aqueous and organic phases.

U.S. Pat. No. 7,317,116 discloses an method for utilizing an industrially convenient fructose source for a dehydration reaction converting a carbohydrate to a furan derivative.

Huang R et al., 2010, Chem. Comm., 46, 1115-1117 discloses integrating enzymatic and acid catalysis to convert glucose into 5-hydroxymethylfurfural.

In the industrial manufacture of high-fructose corn syrup, glucose is often converted into fructose by a process catalyzed by the enzyme xylose isomerase (E.C. 5.3.1.5) which for these reasons is usually called a "glucose isomerase".

Glucose can be isomerized to fructose in a reversible reaction. Under industrial conditions, the equilibrium is close to 50% fructose. To avoid excessive reaction times, the conversion is normally stopped at a yield of about 45% fructose.

Glucose isomerase is one of the relatively few enzymes that are used industrially in an immobilized form. One reason for immobilization is to minimize the reaction time in order to prevent degradation of fructose to organic acids and carbonyl compounds that inactivate the enzyme.

The substrate to the GI-columns is highly purified to avoid clogging of the bed and destabilization of the enzyme. The recommended conductivity is <50 µS/cm.

A description of the most commonly used glucose isomerases is given in table 1 below. The description is based on literature and information from the manufactures and do not necessarily have to be a description of the exact methods used.

TABLE 1

| Manufacturer | Trade name | Enzyme source | Immobilization method |
|---|---|---|---|
| Novozymes A/S | Sweetzyme IT | S. murinus | Crosslinking of cell material with glutaraldehyde, extruded |
| Genencor International | GENSWEET | S. rubigonosus | The enzyme is cross linked with or without cellular debris using PEI (polyethylene imine) and glutaraldehyde. Granular particles are formed by extrusion/marumerization. |
| Godo Shusei | AGI-S-600 | S. griseofuseus | Chitosan-treated glutaraldehyde crosslinked cells, granulated. |

Another way of producing fructose is by hydrolysis of sucrose to obtain a composition comprising glucose and fructose in a 50:50 ratio.

A further way of producing fructose is by catalytic conversion of mannose with mannose isomerase to fructose.

SUMMARY OF THE INVENTION

The invention provides a first method for producing 5-hydroxymethylfurfural comprising
 i) Subjecting a composition comprising fructose to a process in a reactor comprising a reaction medium, wherein said reaction medium comprises an aqueous phase and an organic phase, and wherein said aqueous phase comprises a salt and has a pH in the range of 1.0-10.

In one embodiment step i) may alternatively be
 i) Subjecting a composition comprising fructose to a process in a reactor comprising a reaction medium, wherein said reaction medium comprises an aqueous phase and an organic phase, and wherein said aqueous phase comprises a salt, and wherein the reaction medium does not comprise an acidic catalyst or does not comprise a strong acid.

The invention also provides a second method of producing 5-hydroxymethylfurfural comprising
 x) Subjecting a composition comprising glucose to an enzymatic reaction catalyzed by glucose isomerase, or subjecting a composition comprising mannose to an enzymatic reaction catalyzed by mannose isomerase
 y) Subjecting a composition comprising fructose to a process in a reaction comprising a reaction medium, wherein said reaction medium comprises an aqueous phase and an organic phase and where said aqueous phase comprises a salt.

Steps x) and y) may be performed in any order.

In one embodiment the second method of the present invention comprises:

I) Subjecting a composition comprising glucose to an enzymatic reaction catalyzed by glucose isomerase, or subjecting a composition comprising mannose to an enzymatic reaction catalyzed by mannose isomerase II) Subjecting the composition obtained in step I) to a process in a reactor comprising a reaction medium, wherein said reaction medium comprises an aqueous phase and an organic phase and wherein said aqueous phase comprises a salt.

In another embodiment the second method of the present invention comprises

A) subjecting a composition comprising fructose and glucose, or a composition comprising fructose and mannose, to a process in a reactor comprising a reaction medium, wherein said reaction medium comprises an aqueous phase and an organic phase and wherein said aqueous phase comprises a salt, B) removing glucose or mannose from the reactor in step A), and C) converting the glucose or mannose obtained in step B) to
a) hydroxymethylfurfural, or
b) fructose by an enzymatic reaction catalyzed by glucose isomerase or man nose isomerase.

Furthermore, the present invention also relates to the use of 5-hydroxymethylfurfural obtained by a method according to the present invention.

DEFINITIONS AND ABBREVIATIONS

Figure 1:
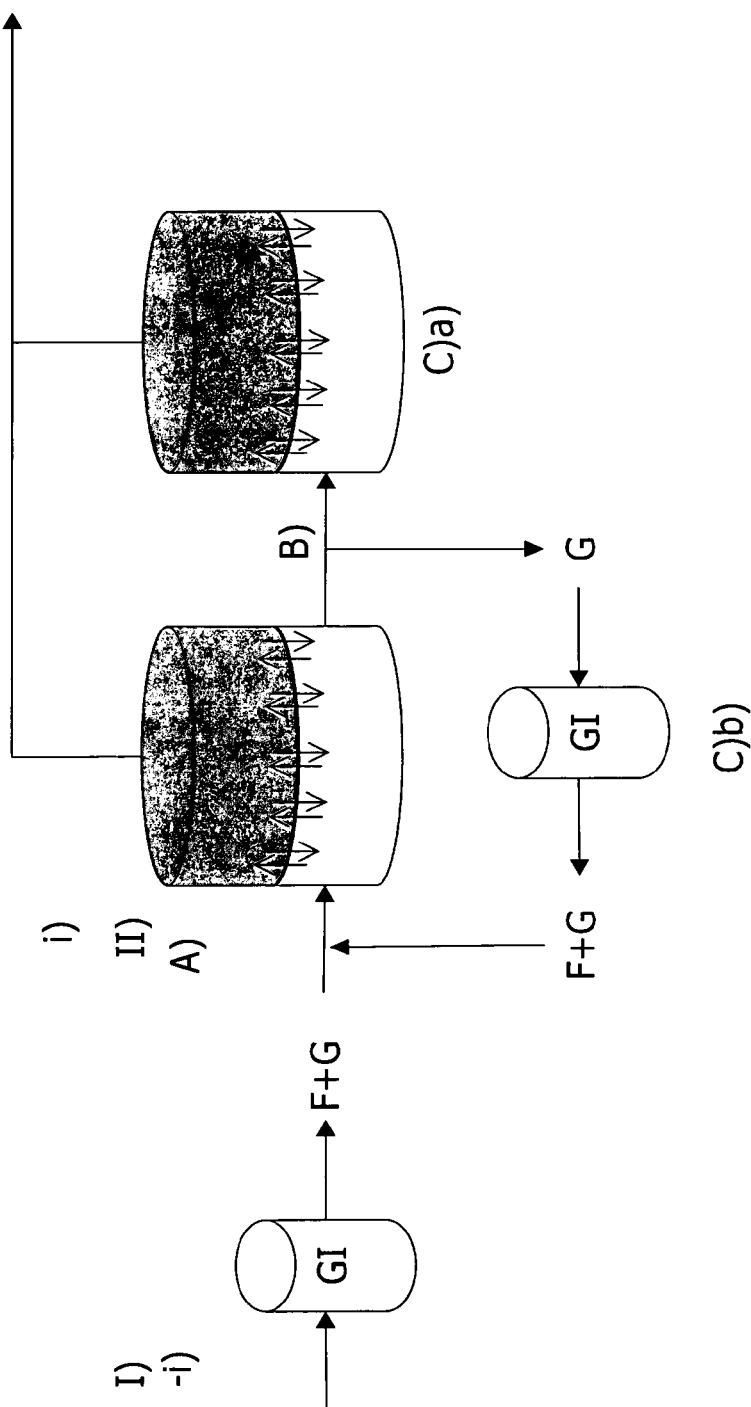
FIG. 1 shows a schematic drawing of the process wherein some of the relevant steps are indicated. GI indicates an immobilized glucose isomerase reactor, G and F indicates glucose and fructose, respectively.

The terms "5-hydroxymethylfurfural", "hydroxymethylfurfural" and "HMF" may be used interchangeably in the context of the present invention. The IUPAC term of HMF is 5-(hydroxymethyl)-2-furaldehyde and it may also be used in the present context.

The term "enzymatic reaction" refers in the context of the present invention to a chemical reaction catalyzed by an enzyme, where "chemical reaction" refers to the general understanding of this term as a process of transforming one or more chemical substances into one or more other chemical substances.

The term "glucose isomerase" refers in the context of the present invention to an enzyme of E.C. 5.3.1.5 which is capable of catalysing the transformation of D-xylose to D-xylulose. Such enzymes are generally used in the high corn syrup industry to convert glucose into fructose. In the context of the present invention glucose isomerase may be abbreviated to "GI" which is intended to encompass any glucose isomerase, e.g. independent of whether it is immobilized or not. As the currently available glucose isomerases are typically immobilized the term "IGI" may also be used which in the context of the present invention is intended to mean "immobilized glucose isomerase".

The term "mannose isomerase" refers in the context of the present invention to an enzyme of E.C. 5.3.1.7 which is capable of catalysing the transformation of D-mannose to D-fructose, The term "saccharide" refers in the context of the present invention to its well known meaning as an organic compound with the general formula $C_m(H_2O)_n$ also known as a carbohydrate. Thus the term "saccharide" includes monosaccharides, disaccharides, oligosaccharides and polysaccharides.

The term "HFCS" refers in the context of the present invention to High Fructose Corn Syrup.

DETAILED DESCRIPTION OF THE INVENTION

Methods of the Present Invention

The present invention relates to methods of producing 5-hydroxymethylfurfural (HMF) by dehydration of fructose and/or glucose, or alternatively fructose and/or mannose. In the following slightly different methods are described which however all relate to the same general concept of producing HMF from fructose and/or glucose, or alternatively fructose and/or mannose. These methods may also be seen as different steps of an overall method which may comprise the steps of each of the methods.

Although, the methods are described individually below the steps of each method may be combined with steps from any of the other methods and the embodiments and examples given with respect to one method may also be used in any of the other methods.

First Method of the Present Invention

Step i)

A first aspect of the present invention relates to a method of producing 5-hydroxymethylfurfural comprising
  i) Subjecting a composition comprising fructose to a process in a reactor comprising a reaction medium, wherein said reaction medium comprises an aqueous phase and an organic phase, and wherein said aqueous phase comprises a salt and has a pH in the range of 1.0-10.

Step i) results in dehydration of fructose to 5-hydroxymethylfurfural. The inventors of the present invention have surprisingly found that salt alone is capable of catalysing this dehydration of fructose to HMF. It is therefore not necessary to add an acidic catalyst to the aqueous phase of the reaction medium which has previously been used to catalyze dehydration of fructose to HMF. Thus in a particular embodiment of step i) the reaction medium does not comprise an acidic catalyst or does not comprise a strong acid.

This has of course the advantage of avoiding handling of strong acids in the manufacturing process. Other advantages are described below, e.g. in relation to steps iii) and iv).

Hence in another embodiment the above mentioned step i) may optionally be
  i) Subjecting a composition comprising fructose to a process in a reactor comprising a reaction medium, wherein said reaction medium comprises an aqueous phase and an organic phase, wherein said aqueous phase comprises a salt, and wherein the reaction medium does not comprise an acidic catalyst or does not comprise a strong acid.

In the context of the present invention "does not contain an acidic catalyst" means that no acidic catalyst has been added to the reaction medium. An "acidic catalyst" may in particular be an acid which has a $pK_a$-value below 5, such as a $pK_a$-value below 4, or a $pK_a$-value below 3, or a $pK_a$-value below 2, or have a $pK_a$-value between 1-5, such as between 1-4, or between 1-3 or between 1-2, or between 1-1.5, or between 2-4, such as between 2-3, or between 2.5-3.5; or between 1.5-4, such as between 1.5-3, or between 1.5-2.5; or between 3-5, such as between 3.5-4.5 or between 3-4, or between 4-5. An "acidic catalyst" may in particular be a "strong acid", wherein a strong acid is an acid with a $pK_a$-value below 1. The term "does not comprise a strong acid" means that no acids with a $pK_a$-value below 1 has been added to the reaction medium; i.e. "a strong acid" is in the context of the present invention to be understood as an acid with a $pK_a$-value which is lower than 1 ($pK_a$(strong acid)<1). It does not exclude the presence of acidic compounds which may be formed as by-products of the dehydration process. Examples of such acidic catalysts include but are not limited to mineral acids, such as HCl, $HNO_3$, $H_2SO_4$, $H_3PO_4$, sulfonic acid, sulfonic acid resins, zeolites, acid-functionalized Mobil composition materials (MCM's), sulphated zirconia, heteropolyacids, phosphates such as $NbOPO_4$, vanadium phosphate, solid silica- and silica-alumina, Brøndsted or Lewis acid catalyst.

The solubility of fructose in the aqueous phase of the reaction medium is much higher than in the organic phase of the reaction medium so the concentration of fructose will generally be much higher in the aqueous phase than in the organic phase of the reaction medium. The dehydration of fructose to 5-hydroxymethylfurfural mainly takes place in the aqueous phase. Some of the HMF may diffuse into the organic phase. This division of HMF between the organic phase and the aqueous phase may described by the partition coefficient, R, where R=(concentration of HMF in organic phase)/(concentration of HMF in aqueous phase). The identity of the organic solvent and the concentration of salt in the aqueous phase affect the value of R. However, in the context of the present invention R may typically be at least 0.8 (R≥0.8), such as at least 0.9 (R≥0.9), or at least 1 (R≥1), or at least 1.1 (R≥1.1), or at least 1.2 (R≥1.2), or at least 1.3 (R≥1.3), or at least 1.4 (R≥1.4), in particular R may be at least 1.5 (R≥1.5) or R may be at least 2 (R≥2).

Once fructose has been dehydrated into HMF, HMF can undergo rehydration thereby producing levulinic acid and/or formic acid. The diffusion of HMF from the aqueous phase into the organic phase is an advantage in order to protect HMF from rehydration.

The presence of salt in the aqueous phase also has the further advantage of decreasing the solubility of HMF in the aqueous phase whereby the equilibrium between HMF in the aqueous phase versus HMF in the organic phase is further shifted towards HMF in the organic phase. Another advantage is that diffusion of HMF into the organic phase protects HMF from rehydration thus the presence of salt results also in protection of HMF from rehydration.

The physical parameters of step i), such as the period of time the reaction takes place, the temperature and the pressure each affect the yield and selectivity of HMF. However, these parameters also affect each other. Thus for example at high temperature the same yield of HMF may be obtained in a shorter period of time than at lower temperatures. Thus the examples of relevant reaction times, temperatures and pressures given in the following does not exclude other examples and they may be combined depending on for example some of the other reaction parameters.

For example step i) described above may be carried out for a period of between 1 second to 20 hours, such as between 1 second to 15 hours, or between 1 second to 10 hours, or between 15 seconds to 20 hours, or between 15 seconds to 15 hours, or between 15 seconds to 10 hours, or between 30 seconds to 20 hours, or between 30 seconds to 15 hours, or between 30 seconds to 10 hours, or between 45 seconds to 20 hours, or between 45 seconds to 15 hours, or between 45 seconds to 10 hours, or between 1 minute to 20 hours, or between 1 minute to 15 hours, or between 1 minute to 10 hours, or between 1 minute to 8 hours, or between 1 minute to 6 hours, or between 30 minutes to 8 hours, or between 30 minutes to 6 hours, or between 30 minutes to 5 hours, or between 45 minutes to 4.5 hours, such as between 40 minutes to 80 minutes, such as for 1 hour, or between 1 to 2 hours, such as for 1.5 hours, or between 100 minutes to 140 minutes, such as for 2 hours, or between 130 minutes to 170 minutes, such as for 2.5 hours, 160 minutes to minutes, such as for 3 hours, or between 190 minutes to 230 minutes, such as for 3.5 hours, or between 220 minutes to 260 minutes, such as for 4 hours, or between 1.5 hours to 4.5 hours.

Furthermore, step i) may be carried out at a temperature in the range of 70-300° C., such as between 70-280° C., or between 70-260° C., or between 70-250° C., or between 80-280° C., or between 80-260° C., or between 80-250° C., or between 90-280° C., or between 90-260° C., or between 90-250° C., or between 140-220° C., or between 140-210° C., or between 150-220° C., or between 150-210° C., or between 160-220° C., or between 160-210° C., or between 170-220° C., or between 170-210° C., or between 180-220° C., or between 180-210° C., or between 180-200° C., or between 110-190° C., or between 110-180° C., or between 110-170° C., or between 110-160° C., or between 120-190° C., or between 120-180° C., or between 120-170° C., or between 120-160° C., or between 125-190° C., or between 125-180° C., or between 125-170° C., or between 125-160° C. or between 130-190° C., or between 130-180° C., or between 130-170° C. or between 130-160° C., or between 130-150° C., such as between 135-145° C., or between 140-160° C., such as between 145-155° C., or between 150-170° C., such as between 155-165° C. Thus the temperature may in one embodiment be around 150° C., 160° C., 170° C., 180° C., 190° C. or 200° C.

The inventors of the present invention have also shown that the HMF yield and HMF selectivity is increased when the temperature is raised and that a high HMF yield and HMF selectivity is maintained at high temperatures (examples 20 and 21).

Typically step i) may be carried out at a pressure ranging between 1 and 200 atm.

In one embodiment step i) may be carried out as a continuous process. In the context of the present invention the term "continuous process" refers to a process which it is not taking place within any defined period of time. The product of such processes is generally also removed continuously from the process. Batch processes are in contrast to continuous processes typically carried out for a specified period of time after which the product is removed from the process.

Thus it is more relevant to characterise continuous processes by a mean residence time. In the context of the present invention the mean residence time may in particular be in the range of 1 second to 2 hours, such as in the range of 30 seconds to 1 hour, or in the range of 45 seconds to 1 hour, or in the range of 45 seconds to 45 minutes, or in the range of 45 seconds to 30 minutes, or in the range of 1-30 minutes, or in the range of 1-25 minutes, or in the range of 1-20 minutes or in the range of 0.5 to 2 hours. The residence time may also be in the range of 1.5-2.25 minutes, e.g. 1.875 minutes, or in the range of 3-5 minutes, e.g. 3.75 minutes, or in the range of 6-9 minutes, e.g. in the range of 7-8 minutes, e.g. 7.5 minutes, or in the range of 13-17 minutes, e.g. in the range of 14-16 minutes, such as 15 minutes. Generally the shorter residence time the better.

The process of step i) takes place in a reactor. In the context of the present invention the term "reactor" refers in principle to any type of container suitable for carrying out the dehydration of fructose and/or glucose and/or mannose to HMF. Examples of suitable containers are well known to a person skilled in the art and include but are not limited to both those suitable for industrial production and those suitable for lab scale processes.

The composition comprising fructose used in step i) may be any composition comprising fructose.

Fructose is on an industrial scale often manufactured by conversion of glucose to fructose which due to the chemical equilibrium of this conversion typically results in a composition comprising approximately 45 w/w % fructose and 55 w/w % glucose.

Another way of producing fructose is by conversion of mannose to fructose which may in particular be carried out by enzymatic catalyzation by mannose isomerase. A composition resulting from this process may then be used in step i) of the present invention. An industrial source of mannose may for example be palm kernel cake.

Another way of obtaining a composition comprising fructose and glucose is by hydrolysis of sucrose which results in a mixture of fructose and glucose in a 50:50 ratio also called inverted sugar syrup. The hydrolysis of sucrose to fructose and glucose may for example be catalyzed by invertase (E.C. 3.2.1.26). This combination of fructose and glucose may then be used in step i) of the method. These compositions comprising both fructose and glucose may be used as a composition comprising fructose in step i). In general compositions comprising high amounts of fructose; e.g. at least 40% w/w fructose, such as HFCS or invert syrup may be used directly in step i) of the process without first subjecting the composition to an enzymatic reaction catalyzed by glucose isomerase, or an enzymatic reaction catalyzed by mannose isomerase, i.e. step —i).

In principle compositions with lower levels of fructose may also be used, however for the process to be economical it is an advantage that the amount of fructose is at least 40% w/w. These compositions may be further purified with respect to fructose to yield a composition comprising from around 55 w/w % to 95 w/w % fructose and from around 45 w/w % or less glucose. Thus in one embodiment of step i) the composition comprising fructose may further comprise glucose or mannose.

Steps —i) and —ii)

If a composition comprising fructose and glucose, or a composition comprising fructose and mannose, is used in step i) the first method of the present invention may in particular comprise a further step preceding step i), e.g. step —i) subjecting a composition comprising glucose to an enzymatic reaction catalyzed by glucose isomerase, or subjecting a composition comprising mannose to an enzymatic reaction catalyzed by mannose isomerase. Examples of methods of such enzymatic catalyzed reactions include but are not limited to those described in Bholand S H et al., Microbiological Reviews, 1996, 60(2), 280-300 and Pedersen S, Bioprocess Technology, 1993, 16, 185-208.

Step —i) may be performed similarly to step iv) b) as described below with the exception that the starting material for the two steps are different.

In another embodiment, step i) may be preceded by another step —ii) hydrolysis of sucrose.

Thus the first method of the present invention may relate to a method of producing 5-hydroxymethylfurfural comprising the steps
—i) and i) or —ii) and i).

With respect to step —i) the embodiments and examples described below in relation to step iv) b) may also be used in step —i).

Step ii)

In one embodiment the first method of the present invention may further comprise a step of
  ii) Removing 5-hydroxymethylfurfural from the reactor in step i).

An advantage of removing 5-hydroxymethylfurfural (HMF) from the reactor in step i) is that the HMF is protected from rehydration into levulinic acid and formic acid.

Step ii) may in particular also be carried out as a continuous process. The advantage of carrying out the process as a continuous process is by continuously removing HMF from the reactor in step i) it is possible to have a continuous production of HMF in step i). If the method is carried out continuously a composition comprising fructose may also be continuously fed into the process prior to step i).

Carrying out the method continuously may in particular be relevant for industrial production of HMF.

If the method of the present invention is performed as a so called batch process meaning that after a certain period of time the process is stopped HMF may simply be removed from the reactor by removing the organic phase of the reaction medium from the reactor.

For continuous processes, the HMF may be removed from the reactor by including a loop into the process in which the organic phase of the reaction medium in step i) is recycled. This recycling step may in particular include a step of removal of HMF from the organic phase. Thus in practice the recycling loop involves continuously removing part of the organic phase from the reaction medium in step i), removing HMF from the organic phase which has been removed from the reactor, and then recycling the remaining part of the organic phase into the reactor in step i).

Methods of removing HMF from the organic phase includes known methods for removing HMF from an organic medium and may for example be performed by back extraction, evaporation of solvent, thin film evaporation, wiped film evaporation, chromatography, distillation, adsorption to an inert adsorbent, counter current extraction or any other means of product recovery that is known to a person skilled in the art.
Steps iii) and iv)

If the composition of step i) comprises fructose and glucose, or fructose and mannose, then the glucose or mannose may in particular be converted to either HMF or fructose. Although, glucose or mannose may be converted to HMF directly in the reactor, such as described in examples 3 and 4, the glucose or mannose may in a particular embodiment be removed from the reactor prior to converting it to HMF or fructose. Thus the process may in this embodiment further comprise the steps of iii) Removing glucose or mannose from the reactor in step i), and iv) Converting the glucose or mannose obtained in step iii) to
 a) Hydroxymethylfurfural, or
 b) Fructose by an enzymatic reaction catalyzed by a glucose isomerase or a mannose isomerase.

Steps iii) and iv) may be carried out in combination with step i), steps —i) and i), steps —ii) and i) or in combination with steps i) and ii), steps —i), and i), steps —i), i) and ii), steps —ii) and i) or steps —ii), i) and ii).

Any of steps i), ii), iii), and iv) or any combination thereof may be carried out in an inert atmosphere such as in an argon or nitrogen atmosphere. The advantage of an inert atmosphere is generally that it reduces oxidation and thereby avoids production of too many unwanted side-products.

If step i) and/or the whole process is non-continuous the fructose used in step i) is converted to HMF in step i) and extracted into the organic phase of the reaction medium in step i). In contrast to this most of the glucose or mannose present in the composition comprising fructose and glucose, or fructose and mannose, respectively, is left unreacted in the aqueous phase of the reaction medium. Thus if step i) and/or the whole process is non-continuous step iii); i.e. removing glucose or mannose from the reactor in step i) may simply be carried out by removing the aqueous phase of the reaction medium.

If step i) and/or the whole process are continuous methods step iii) may generally be performed by continuously removing part of the aqueous phase from the reactor. Such methods are well known for a person skilled in the art.

Step iv) a) converting the glucose or mannose obtained in step iii) to 5-hydroxymethylfurfural may be analogous to the process of converting fructose to HMF; e.g. it may similarly to step i) be carried out by subjecting the glucose or mannose to a process in a reactor comprising a reaction medium, wherein said reaction medium comprises an aqueous phase and an organic phase and wherein said aqueous phase comprises a salt. The process of converting glucose or mannose to HMF may thereby take place in a different reactor than the process of converting fructose to HMF. However, the conditions which are optimal for converting fructose to HMF are not necessarily all the same as those which are optimal for converting glucose or mannose to HMF. Hence in the following those conditions of step iv) a) which may differ from those of step i) are described.

The aqueous phase of the reaction medium of step iv) a) may in particular have a pH in the range of 1 to 9, such as a pH in the range of 1 to 8, or in the range of 1 to 7, or in the range of 1 to 6, or in the range of 1 to 5, or in the range of 1 to 4, or in the range of 1.5 to 8, or in the range of 1.5 to 7, or in the range of 1.5 to 6, or in the range of 1.5 to 5, or in the range of 1.5 to 4. Furthermore, the reaction medium of step iv) a) may in a particular embodiment comprise an acidic catalyst such as $AlCl_3$. Even though, some of the reaction conditions for step iv) a) may differ from those of step i) the choice of salt, temperature, periods of time etc, described in relation to step i), may also be used in relation to step iv) a).

Examples 3 and 4 describe one way of carrying out a method of the present invention comprising steps i), ii) and iv) a), and steps i) and iv) a), respectively. Thus if the method of the present invention comprises steps i) and iv) a) it may further in one embodiment also comprise a step of cooling between steps i) and iv) a). Furthermore, as shown in examples 3 and 4 it is an advantage to replace the organic phase of the reaction medium in step i) with a new organic phase in the reaction medium of step iv) a) as this increases the yield of HMF. In this context the term "new" refers to fresh meaning that the chemical composition of the organic phase of the reaction medium used in step i) may be the same as that of the organic phase of the reaction medium used in step iv) a).

The present invention describes two different steps of converting glucose or mannose to fructose by an enzymatic reaction catalyzed by a glucose isomerase or a mannose isomerase, i.e. steps —i) and iv) b). These two steps are in principle the same step with the exception that the starting material for these steps is different. The starting material for the step preceding step i), step —i), may be glucose or mannose obtained from generally any suitable source while the glucose or mannose used in step iv) b) is obtained from step iii) of the process; i.e. it is removed from the reactor in which fructose is converted to HMF. Thus the composition comprising glucose or mannose used in step iv) b) may for example comprise any combination of the following components; HMF, organic solvent from the organic phase of the reaction medium and side-products, such as humins, soluble polymers, levulinic acid and formic acid produced in step i). In the context of the present invention the term "humin" or "humins" refer to insoluble or non-soluble polymers. Some of the components, e.g. the insoluble humins, may block the immobilized glucose isomerase reactor or affect the functionality of mannose isomerase. Thus in a particular embodiment one or more of these compounds may be removed from the composition comprising glucose or mannose prior to subjecting it to the glucose isomerase or mannose isomerase; i.e. step iv) b). Hence the method may further comprise a step between steps iii) and iv) b) comprising removing one or more components. For example the method may in one embodiment comprise a step of removing humins between steps iii) and iv) b). For industrial purposes the non-soluble humins may typically be removed by filtration. The sugars, i.e. glucose and/or fructose and/or mannose, used in the present invention may be obtained by saccharification of starch. In this case the soluble polymers may be recycled in the process by adding them to the step of starch saccharification.

The glucose or mannose withdrawn from the reactor in step iii) may be withdrawn as an aqueous solution and it may therefore be relevant to remove some of the water prior to subjecting it to the glucose isomerase or mannose isomerase in step iv). This may for example be performed by evaporation.

The step of converting glucose or mannose to fructose by an enzymatic reaction catalyzed by a glucose isomerase or mannose isomerase is in the present context not limited to any particular method.

Currently the glucose isomerases used on an industrial scale are immobilised glucose isomerase, in particular glucose isomerase (GI) based on a glutaraldehyde crosslinked cell material, although columns with GI immobilized on ion exchange resins as carrier material are also known. However, the methods of the present invention are not limited to the use of immobilised glucose isomerases. Thus it is foreseen that also non-immobilized glucose isomerase may be used in the present invention.

Examples of suitable glucose isomerases which may be used in the present invention include glucose isomerase from *S. murinus, S. rubigonosus* or *S. griseofuseus* which in particular may be immobilized by crosslinking of cell material with glutaraldehyde. Examples of such commercially available immobilized glucose isomerases include but are not limited to Sweetzyme from Novozymes A/S or Gensweet from Genencor International or AGI-S-600 from Godo Shusei.

The process conditions for use of the glucose isomerase to convert glucose to fructose depend on e.g. the starting material and the particular glucose isomerase. Such conditions are well known for a person skilled in the art. For example borate may be present to boost the fructose equilibrium. The inventors of the present invention have surprisingly found that high concentrations of salt stabilize the immobilized glucose isomerase. Thus the inventors of the present invention has found that the functionality of glucose isomerase is not affected under conditions where the conductivity is in the range of 6-25 mS/cm, which is approximately 100 times higher than the conductivity of 50 μS/cm which is generally recommended for glucose isomerase.

As the aqueous phase of the reaction medium in step i) comprises high salt concentrations the composition comprising glucose or mannose obtained in step iii) of the present invention also comprises a high concentration of salt. Glucose isomerase are generally used under conditions where the salt concentration is lower than that of the composition comprising glucose obtained in step iii) of the present method. It was therefore a surprise that the inventors of the present invention found that the high concentration of salt in the composition comprising glucose obtained in step iii) did not affect the functionality of the glucose isomerase in step iv) b) of the method. Typically current recommendations for the use of glucose isomerase is that the conductivity is <50 μS/cm, while the inventors of the present invention found that the functionality of glucose isomerase (Sweetzyme™) may be as high as 6-25 mS/cm as shown in example 12. Furthermore it actually appeared that the high salt concentration with NaCl further stabilised the glucose isomerase. In the case with KCl and $Na_2SO_4$ the glucose isomerase performance was comparable with a normal glucose substrate without the addition of extra salts.

For step iv) b) the starting material is glucose or mannose removed from the reactor in step i), which is generally the aqueous phase or part of the aqueous phase of the reaction medium in step i). The aqueous phase of the reaction medium may become acidic due to e.g. levulinic acid and formic acid which may often form as by-products of the process of dehydration of fructose to HMF. Thus the composition comprising glucose or mannose which is removed from the reactor in step iii) may be acidic, i.e. with a pH below 7. Glucose isomerase typically works optimally at a pH in the range of 6-9 thus the pH of the composition comprising glucose obtained in step iii) may in a particular embodiment be adjusted to a pH in the range of 6-9 prior to performing step iv) b). This may be similarly relevant if the composition obtained in step iii) comprises mannose. Examples of suitable bases for adjusting the pH include but are not limited to $Na_2CO_3$ and NaOH. An advantage of the present invention is that the inventors of the present invention have found that it is not necessary to use an acidic catalyst in step i) of the method. This reduces the need to add base to the composition comprising glucose or mannose obtained in step iii) of the method prior to subjecting it to glucose isomerase or mannose isomerase in step iv) b). Furthermore, another advantage of avoiding the acidic catalyst or avoiding using a strong acid as catalyst, in the reaction medium of step i) in this embodiment is that when pH is adjusted to a higher pH it generally also results in an increase of the salt concentration. Although, the inventors of the present invention have found that glucose isomerase functions at higher salt concentrations than previously anticipated too high salt concentrations, such as higher than 25 w/w % as indicated in example 12, may still affect the functionality of the glucose isomerase adversely. In this case it would therefore be necessary to remove some of the salt from the composition comprising glucose which is withdrawn from the reactor prior to subjecting it to the glucose isomerase. Thus by avoiding acidic catalysts or avoiding using strong acids as catalysts, in the reaction medium of step i) no or at least less salt has to be removed from the composition comprising glucose or mannose obtained in step iii) prior to subjecting it to step iv) b).

The fructose obtained from step iv) b) may further be subjected to step i) thereby creating a loop in the method where glucose or mannose removed from step i) is converted to fructose in step iv) b) which is then subsequently converted to HMF in step i). Thus the above mentioned process may in a particular embodiment comprise a further step of v) Subjecting the fructose obtained in step iv) b) to the process of step i).

The advantage of including steps iii), iv) b) and v) in the method of the present invention, i.e. removing glucose or mannose from the reactor in step i) and converting it to fructose which is then subsequently re-introduced in step i) is that based on the starting material used in step i) the relative yield of HMF is higher than if e.g. the glucose or mannose is not recycled. Furthermore, step iv) b) also has the advantage of creating less unwanted side-products such as humins, than step iv) a) which is the conversion of glucose or mannose to HMF.

Embodiments of the First Method

Thus a method according to the present invention may comprise the steps of
i) Subjecting a composition comprising fructose to a process in a reactor comprising a reaction medium, wherein said reaction medium comprises an aqueous phase and an organic phase, and wherein said aqueous phase comprises a salt and has a pH in the range of 1.0-10.

In another embodiment the method according to the present invention comprises the steps of
i) Subjecting a composition comprising fructose to a process in a reactor comprising a reaction medium, wherein said reaction medium comprises an aqueous phase and an organic phase, and wherein said aqueous phase comprises a salt and has a pH in the range of 1.0-10.
ii) Removing 5-hydroxymethylfurfural from the reactor in step i).

In yet another embodiment the method according to the present invention may comprise the steps of
i) Subjecting a composition comprising fructose to a process in a reactor comprising a reaction medium, wherein said reaction medium comprises an aqueous phase and an organic phase, and wherein said aqueous phase comprises a salt and has a pH in the range of 1.0-10.
ii) Removing 5-hydroxymethylfurfural from the reactor in step i).
iii) Removing glucose or mannose from the reactor in step i), and
iv) Converting the glucose or mannose obtained in step iii) to
  a) Hydroxymethylfurfural, or
  b) Fructose by an enzymatic reaction catalyzed by a glucose isomerase or a mannose isomerase.

In yet another embodiment the method according to the present invention may comprise the steps of
i) Subjecting a composition comprising fructose to a process in a reactor comprising a reaction medium, wherein said reaction medium comprises an aqueous phase and an organic phase, and wherein said aqueous phase comprises a salt and has a pH in the range of 1.0-10.
iii) Removing glucose or mannose from the reactor in step i), and
iv) Converting the glucose or mannose obtained in step iii) to
  a) Hydroxymethylfurfural, or
  b) Fructose by an enzymatic reaction catalyzed by a glucose isomerase or a mannose isomerase.

In any of the above mentioned methods step i) may alternatively be
i) Subjecting a composition comprising fructose to a process in a reactor comprising a reaction medium, wherein said reaction medium comprises an aqueous phase and an organic phase, wherein said aqueous phase comprises a salt, and wherein the reaction medium does not comprise an acidic catalyst or does not comprise a strong acid.

Any of the above described methods may further comprise step —i) or step —ii) as described above.

Furthermore, as also described above those processes comprising step iv) b) may also in a further embodiment comprise the above mentioned step v).

The methods of the present invention may be carried out as continuous processes or as batch processes.

Second Method of the Present Invention

A second aspect of the present invention relates to a method of producing HMF comprising
x) Subjecting a composition comprising glucose to an enzymatic reaction catalyzed by glucose isomerase, or subjecting a composition comprising mannose to an enzymatic reaction catalyzed by a mannose isomerase
y) Subjecting a composition comprising fructose to a process in a reactor comprising a reaction medium, wherein said reaction medium comprises an aqueous phase and an organic phase and where said aqueous phase comprises a salt.

Steps x) and y) may be performed in any order.

In one embodiment the second method of the present invention may comprise
I) Subjecting a composition comprising glucose to an enzymatic reaction catalyzed by glucose isomerase, or subjecting a composition comprising mannose to an enzymatic reaction catalyzed by a mannose isomerase
II) Subjecting the composition obtained in step I) to a process in a reactor comprising a reaction medium, wherein said reaction medium comprises an aqueous phase and an organic phase and wherein said aqueous phase comprises a salt.

This process may in one embodiment further comprise the steps of
III) Removing glucose or mannose from the reactor in step II), and
IV) Converting glucose or mannose obtained in step III) to
  a) Hydroxymethylfurfural, or
  b) Fructose by an enzymatic reaction catalyzed by glucose isomerase or mannose isomerase.

Step x) is the same as step —i) described above. Thus the embodiments described in relation to the step —i) may apply mutatis mutandis to step x).

Step y) is similar to step i) described above with the exception that a pH step is not defined in step y). The embodiments, examples and reaction conditions described in relation to step i) may apply mutatis mutandis to step y).

Step I) is the same as the step —i) described above. Thus the embodiments described in relation to the step —i) may apply mutatis mutandis to step I).

Step II) is similar to step i) described above with the exception that a pH range is not defined in step II). In a particular embodiment the pH of the aqueous phase of the reaction medium in step II) may be in the range of 1.0 to 10. The embodiments, examples and reaction conditions described in relation to step i) may apply mutatis mutandis to step II).

Step III) is similar to step iii) described above and the embodiments, examples and reaction conditions described in relation to step iii) may apply mutatis mutandis to step III).

The step of converting glucose or mannose to HMF; i.e. step IV) a) may in particular comprise subjecting the glucose or mannose to a process in a reactor comprising a reaction medium, wherein said reaction medium comprises an aqueous phase and an organic phase and wherein said aqueous phase comprises a salt. In this embodiment the aqueous phase may in particular have a pH in the range of 1-9.

Step IV) a) is similar to step iv) a) above and the embodiments, examples and reaction conditions described in relation to step iv) a) above may apply mutatis mutandis to step IV) a).

Step IV) b) is similar to step iv) b) described above and the embodiments and reaction conditions described in relation to step iv) b) may apply mutatis mutandis to step IV) b).

In another embodiment the second method of the present invention relates to a method of producing HMF comprising
- A) subjecting a composition comprising fructose and glucose, or a composition comprising fructose and mannose, to a process in a reactor comprising a reaction medium, wherein said reaction medium comprises an aqueous phase and an organic phase and wherein said aqueous phase comprises a salt,
- B) removing glucose or mannose from the reactor in step A), and
- C) converting the glucose or mannose obtained in step B) to
  - a) hydroxymethylfurfural, or
  - b) fructose by an enzymatic reaction catalyzed by glucose isomerase or mannose isomerase.

Step A) is similar but not identical to the embodiment of step i) where the composition comprises both glucose and fructose, or both mannose and fructose. However, in a particular embodiment the pH of the aqueous phase of the reaction medium in step A) is in the range of 1.0 to 10. Furthermore, all of the embodiments, examples and reaction conditions described in relation to the embodiment of step i) wherein the composition comprises fructose and glucose, or fructose and mannose, may apply mutatis mutandis to step A).

Step B) is similar to step iii) described above. Hence the embodiments, examples and reaction conditions described in relation to step iii) may apply mutatis mutandis to step B).

Step C) a) is similar to step iv) a) described above and the embodiments, examples and reaction conditions described in relation to step iv) a) may apply mutatis mutandis to step IV) a).

Step C) b) is similar to step iv) b) described above and the embodiments, examples and reaction conditions described in relation to step iv) b) may apply mutatis mutandis to step IV) b). Equipment useful for carrying out these different steps is well known for a person skilled in the art.

Use of HMF

The HMF produced by any of the above mentioned first and second methods may be further processed to obtain another product. Examples of such products include but are not limited to 2,5-furandicarboxylic acid (FDCA), diformylfuran (DFF), formylfuran carboxylic acid (FFCA) and 2,5-dimethylfuran (DMF).

The HMF produced by any of the above mentioned processes may in particular be oxidized to produce 2,5-furandicarboxylic acid, diformylfuran (DFF) or formylfuran carboxylic acid (FFCA). Hence any of the above mentioned methods may comprise a further step of oxidizing the obtained HMF to 2,5-furandicarboxylic acid.

Examples of methods suitable for oxidizing HMF to 2,5-furandicarboxylic acid include but are not limited to those described in US patents U.S. Pat. No. 4,977,283 and U.S. Pat. No. 7,411,078, and US patent application US 2008/0103318.

U.S. Pat. No. 4,977,283 describes a process for the oxidation of 5-hydroxymethylfurfural which comprises oxidizing 5-hydroxymethylfurfural in an aqueous medium with oxygen in the presence of a catalyst which contains at least one metal of the platinum group.

U.S. Pat. No. 7,411,078 describes oxidizing e.g. 5-hydroxymethylfurfural with a metal permanganate in an alkaline environment to produce 2,5-furandicarboxylic acid. Advantageously, the alkaline environment contains at least one of alkali metal hydroxides and alkali earth metal hydroxides, and the oxidation is performed at a temperature of from 1 to 50° C.

US 2008/01003318 describes a method of oxidizing hydroxymethylfurfural (HMF) includes providing a starting material which includes HMF in a solvent comprising water into a reactor. At least one of air and $O_2$ is provided into the reactor. The starting material is contacted with a catalyst comprising Pt on a support material where the contacting is conducted at a reactor temperature of from about 50° C. to about 200° C.

Hence any of the methods of the present invention may comprise as a further step a process of oxidizing HMF to 2,5-furandicarboxylic as described above.

Furthermore, the present invention also relates to the products obtained by any method according to the present invention.

Compositions

The present invention relates to the production of hydroxymethylfurfural by dehydration of fructose and/or glucose.

The methods of the present invention may use different starting materials, i.e. a composition comprising fructose, a composition comprising glucose, a composition comprising mannose, a composition comprising glucose and fructose, or a composition comprising fructose and mannose. As these compositions may have certain features in common the term "starting material" used in the following refers to all compositions; i.e. a composition comprising fructose, a composition comprising glucose, a composition comprising mannose, a composition comprising fructose and glucose, and a composition comprising fructose and mannose. Often such industrially produced compositions comprise different saccharides, such as both glucose and fructose, or both fructose and mannose or even both fructose, glucose and mannose, however the present invention is not limited to such composition as compositions which have been purified with respect to either glucose, mannose or fructose can also be used.

The term "composition" is in the context of the present invention to be understood in its broadest context; however it may typically be an aqueous solution.

The compositions used in the present invention as starting materials, i.e. the composition comprising fructose, the composition comprising glucose, the composition comprising mannose, the composition comprising glucose and fructose, and the composition comprising mannose and fructose, may typically contain a total of at least 20 w/w % glucose, mannose and fructose. The composition comprising fructose, the composition comprising glucose and the composition comprising glucose and fructose may typically contain least 20 w/w % glucose and fructose, such as a total of 30-90 w/w % fructose and glucose, e.g. 40-90 w/w % fructose and glucose, or a total of 50-90 w/w % fructose and glucose, or a total of 60-90 w/w % fructose and glucose, or a total of 70-90 w/w % fructose and glucose, or a total of 80-90 w/w % fructose and glucose. The composition comprising fructose, the composition comprising mannose and the composition comprising fructose and mannose may typically contain least 20 w/w % mannose and fructose, such as a total of 30-90 w/w % fructose and mannose, e.g. 40-90 w/w % fructose and mannose, or a total of 50-90 w/w % fructose and mannose, or a total of 60-90 w/w % fructose and mannose, or a total of 70-90 w/w % fructose and mannose, or a total of 80-90 w/w % fructose and mannose.

As the compositions used as starting materials in the methods of the present invention in many cases may be obtained from natural sources, e.g. biomass, they may also contain other components than fructose and/or glucose and/or mannose including other saccharides. For example the compositions used as starting material in the methods of the present invention may comprise 0-10 w/w % oligosaccharides.

The choice of starting material may to some extent affect the combination of steps in a method of the present invention. Furthermore, the compositions comprising glucose, fructose, mannose, fructose and mannose, or glucose and fructose, used in the methods of the present invention, may as described above comprise other saccharides than fructose, glucose and mannose.

For example if a composition comprises a relative high amount of fructose it may be used directly as a starting material for the dehydration process of fructose to HMF; i.e. in steps i), y), II) and A) of the methods of the present invention. In this context a "relative high amount of fructose" may typically be a composition wherein at least 40 w/w % of the total amount of saccharides in the composition is fructose or that fructose constitutes at least 40 w/w % of the total amount of saccharides in the composition.

Thus the compositions used in steps i), y), II) and A) of the present invention, i.e. a composition comprising fructose, the composition obtained from step I), a composition comprising fructose and mannose, and a composition comprising glucose and fructose may in a particular embodiment be a composition wherein 40-100 w/w % of the total amount of saccharides in the composition is fructose. More particularly 45-100 w/w % of the total amount of saccharides may be fructose, or 45-95 w/w % of the total amount of saccharides may be fructose, or 50-95 w/w % of the total amount of saccharides may be fructose.

Examples of compositions wherein fructose constitutes more than 40 w/w % of the total amount of saccharides present in the composition include but are not limited to HFCS (high fructose corn syrup), invert sugar, inulin and compositions which have been purified with respect to fructose.

HFCS typically comprise 40-60 w/w % fructose of the total amount of saccharides. Moreover, the ratio of fructose to glucose in HFCS is typically between 40:60 and 60:40, such as a ratio between 44:56 and 46:54, more particularly a ratio of 45:55. In some cases the ratio of fructose to glucose in HFCS may be in the range of 53:47 to 59:41, or in the range of 40:60 to 44:56.

Invert sugar also known as inverted sugar syrup, arise from hydrolysis of sucrose and invert sugar therefore typically comprises fructose and glucose in a ratio of approximately between 48:52 and 52:48, such as a ratio between 49:51 and 51:49, more particularly a ratio of 50:50. Thus fructose typically constitute 48-52 w/w % of the total amount of saccharides in invert sugar, in particular 49-51 w/w % of the total amount of saccharides is fructose, even more particularly 50 w/w % of the total amount of saccharides is fructose. Glucose similarly constitute 48-52 w/w % of the total amount of saccharides in invert sugar, in particular 49-51 w/w % of the total amount of saccharides in invert sugar is glucose, even more particularly 50 w/w % of the total amount of saccharides in invert sugar is glucose.

Insulins are polymers that mainly comprises fructose units joined by a β(2→1) glycosidic bond and which typically have a terminal glucose units. Hydrolysis of inulin typically results in a composition wherein approximately 90 w/w %, e.g. in the range of 85-95 w/w %, of the total amount of saccharides is fructose and approximately 10 w/w %, e.g. in the range of 5-15 w/w %, of the total amount of saccharides is glucose.

If on the other hand a composition comprising a relative high concentration of glucose or mannose, and a relative low concentration of fructose is used as a starting material in a method of the present invention it is an advantage to include a step of increasing the amount of fructose relative to the amount of glucose or mannose, prior to using it in the dehydration process of steps i), y), II) and A) of the present inventions. Methods of increasing the amount of fructose in a composition include steps x), I), —i) and —ii) described above but it may also involve other methods such as purification of fructose. In this context a "relative high concentration of glucose or mannose" means a composition wherein 60-100 w/w % of the total amount of saccharides is glucose or mannose, such as 60-95 w/w % of the total amount of saccharides is glucose or mannose.

Furthermore, in this context the term "relative low concentration of fructose" means a composition wherein fructose constitutes 40 w/w % or less than 40 w/w % of the total amount of saccharides, i.e. wherein 0-40 w/w % of the total amount of saccharides is fructose.

Examples of such compositions comprising a high concentration of glucose and a low concentration of fructose include but are not limited to glucose obtained from any source of starch, such as but not limited to corn, wheat and potatoes, glucose obtained from cellulosic biomass, e.g. fibres, stovers, wheat, or straw. The glucose may also be obtained from other sources of starch or biomass known to a person skilled in the art.

Glucose obtained from starch typically results in a composition wherein approximately 92-98 w/w % of the total amount of saccharides is glucose.

Converting glucose to fructose by an enzymatic reaction catalyzed by glucose isomerase, e.g. steps —i), iv) b), x), I), IV) b) and C) b) of the present invention typically results in a composition wherein approximately 43-47 w/w % of the total amount of saccharides is fructose and approximately 53-57 w/w % of the total amount of saccharides is glucose. Thus the ratio of fructose to glucose in these compositions may typically be in range of 43:57 and 47:53, such as in the range of 44:56 and 46:54, or approximately 45:55.

Examples of compositions comprising a high concentration of mannose and a low concentration of fructose include but are not limited to palm kernel cake.

Mannose may in a particular embodiment be converted to fructose by an enzymatic reaction catalyzed by mannose isomerase, e.g. steps —i), iv) b), x), I), IV) b) and C) b) of the present invention.

Reaction Medium

The processes of converting fructose or glucose or mannose to HMF in steps i), y), II), A), iv) a), IV) a) and C) a) take place in a reaction medium comprising an aqueous phase and an organic phase. Thus the reaction medium of the present invention comprises two phases which typically may be liquid phases due to the nature of the components involved and the dehydration process. In the context of the present invention the term "phase" refers to the solubility of the aqueous phase in the organic phase and vice versa. Thus in the context of the present invention it means that the solubility of the aqueous phase in the organic phase and vice versa is so low that the reaction medium comprises two distinct phases; i.e. the aqueous phase and the organic phase.

The term "aqueous phase" means in the context of the present invention that the solvent of the aqueous phase is mainly water. In this respect "mainly water" means that 50-100 v/v % of the solvent of the aqueous phase is water, e.g. 55-100 v/v % of the solvent of the aqueous phase is water, or 60-100 v/v % of the solvent of the aqueous phase is water, or 65-100 v/v % of the solvent of the aqueous phase is water, or 70-100 v/v % of the solvent of the aqueous phase is water, or 75-100 v/v % of the solvent of the aqueous phase is water, or 80-100 v/v % of the solvent of the aqueous phase is water, or 85-100 v/v % of the solvent of the aqueous phase is water, or 90-100 v/v % of the solvent of the aqueous phase is water, or 95-100 v/v % of the solvent of the aqueous phase is water. Thus the aqueous phase of the reaction medium of the present invention comprises in particular less than 50 v/v % other solvents, such as DMSO. Hence the amount of other solvents, including DMSO, than water in the aqueous phase of the reaction medium may in particular be in the range of 0-50 v/v %, more particularly in the range of 0-45 v/v %, or in the range of 0-40 v/v %, or in the range of 0-35 v/v %, or in the range of 0-30 v/v %, or in the range of 0-25 v/v %, or in the range of 0-20 v/v %, or in the range of 0-15 v/v %, or in the range of 0-10 v/v %, or in the range of 0-5 v/v %.

It is particularly relevant that the solvent of the aqueous phase is mainly water when step iv) b), IV) b) or C) b) are present in a method of the present invention because other solvents may affect the functionality of the glucose isomerase or mannose isomerase used in these steps. For example glucose isomerase does not function optimally if DMSO is present. Trace amounts of such unwanted solvents may of course be present. It is just advantageous that the amount of other solvents is not so high that it affects the functionality of the glucose isomerase or mannose isomerase significantly. The amount of solvent which may be present without significantly affecting the functionality of the glucose isomerase or mannose isomerase depends on the particular solvent.

As described above the inventors of the present invention have surprisingly found that salt is capable of catalyzing dehydration of fructose to HMF.

The aqueous phase of the reaction medium comprises a salt. In the context of the present invention the term "salt" is to be understood as an ionic compound composed of cations (positively charged ions) and anions (negative ions) so that the product is electrically neutral (without a net charge). These component ions can be inorganic such as chloride (Cl$^-$), as well as organic such as acetate (CH3COO$^-$) and monoatomic ions such as fluoride (F$^-$), as well as polyatomic ions such as sulfate (SO$_4^{2-}$), or monovalent ions, such as Na$^+$, or divalent ions, such as Mg$^{2+}$. There are several varieties of salts. Salts that produce hydroxide ions when dissolved in water are basic salts and salts that produce hydronium ions in water are acid salts. Neutral salts are those that are neither acid nor basic salts. Zwitterions contain an anionic center and a cationic center in the same molecule but are not considered to be salts. Examples include amino acids, many metabolites, peptides and proteins. When salts are dissolved in water, they are called electrolytes, and are able to conduct electricity, a property that is shared with molten salts.

The presence of salt in the aqueous phase decreases the solubility of HMF in the aqueous phase whereby the equilibrium of HMF between the aqueous phase and the organic phase is shifted towards the organic phase. This results in a further shift in the equilibrium of the dehydration process of glucose and/or fructose to HMF in the aqueous phase towards production of more HMF.

The salt present in the aqueous phase may in particular be an inorganic salt, such as a salt selected from the group consisting of but not limited to metal halides, metal sulphates, metal sulphides, metal phosphates, metal nitrates, metal acetates, metal sulphites and metal carbonates. Examples of such salts include but are not limited to sodium chloride (NaCl), sodium sulphite (Na$_2$SO$_3$), magnesium chloride (MgCl$_2$), lithium chloride (LiCl), potassium chloride (KCl), calcium chloride (CaCl$_2$), cesium chloride (CsCl), sodium sulphate (Na$_2$SO$_4$), potassium sulphate (K$_2$SO$_4$), lithium bromide (LiBr), sodium bromide (NaBr), potassium bromide (KBr), lithium nitrate (LiNO$_3$), sodium nitrate (NaNO$_3$), potassium nitrate (KNO$_3$) and potassium iodine (K$_1$).

The salt may in particular be a metal halide, such as NaCl, MgCl$_2$, LiCl, KCl, CaCl$_2$, CsCl, LiBr, NaBr, KBr or KI.

The concentration of salt may depend on the choice of salt, however it may for many or most salts be in the range of 0.1-30 w/w %, such as in the range of 0.5-30 w/w %, or in the range of 1-30 w/w %, or in the range of 0.1-25 w/w %, or in the range of 0.5-25 w/w %, or in the range of 1-25 w/w %, or in the range of 0.1-20 w/w %, or in the range of 0.5-20 w/w %, or in the range of 1-20 w/w %, or in the range of 0.5-15 w/w %, or in the range of 0.5-10 w/w %, or in the range of 0.5-7.5 w/w %, or in the range of 1-10 w/w %, or in the range of 1-7.5 w/w %, or in the range of 1-5 w/w %, or in the range of 2-10 w/w %, or in the range of 2-7.5 w/w %, or in the range of 2-5 w/w %.

The inventors of the present invention has shown that by combining the salt with a weak acid, such as boric acid, the HMF yield and fructose conversion is increased even further. This is shown in examples 16-19. Without being bound by any theory the inventors of the present invention are of the opinion that the combination of the sugars (e.g. fructose or glucose) and salt may affect the acidic effect of boric acid causing it to behave more acidic than without the presence of sugar and salt.

Hence in a particular embodiment the aqueous phase may comprise a weak acid. In the context of the present invention a weak acid is an acid with a pK$_a$-value which is 1 or higher than 1 (pK$_a$(weak acid)≥1). Examples of such acids include boric acid (B(OH)$_3$). The amount of weak acid, e.g. boric acid, in the aqueous phase may typically be in the range of 0.1-200 g/L, such as in the range of 5-200 g/L, or in the range of, 10-200 g/L, or in the range of 10-150 g/L, or in the range of 25-150 g/L, or in the range of 50-150 g/L, or in the range of 50-125 g/L, or in the range of 75-125 g/L, such as 100 g/L.

Addition of a weak acid such as boric acid to the reaction medium does not decrease the pH as much as when using a strong acid as a catalyst. Thus the advantages of using salt as catalyst compared to using a strong acid also applies to using a combination of salt and a weak acid, such as boric acid, as a catalyst.

For the process of dehydrating fructose to HMF; i.e. steps i), y), II) and A) the aqueous phase of the reaction medium may in a particular embodiment have a pH in the range of pH 1.0 to 10, such as in the range of pH 1.5-10, or in the range of pH 1.6-10, or in the range of pH 1.7-10, or in the range of pH 1.8-10, or in the range of pH 1.9-10, or in the range of pH 2.0-10, or in the range of 2.1-10, or in the range of pH 2.2-10, or in the range of pH 2.3-10, or in the range of pH 2.4-10, or in the range of pH 2.5-10, or in the range of pH 2.6-10, or in the range of pH 2.7-10, or in the range of pH 2.8-10, or in the range of pH 2.9-10, or in the range of pH 3 to 10, or in the range of pH 3 to 9, or in the range of pH 3.5 to 9, or in the range of pH 3 to 8, or in the range of pH 3.5 to 8, or in the range of 4 to 9, or in the range of pH 4 to 8.5, or in the range of pH 4 to 8, or in the range of pH 4.5 to 10, or in the range of pH 4.5 to 9, or in the range of pH 4.5 to 8.5, or in the range of pH 4.5 to 8, or in the range of pH 5 to 10, or in the range of pH 5 to 9, or in the range of pH 5 to 8.5, or in the range of pH 5 to 8, or in the range of pH 5.5 to 10, or in the range of pH 5.5 to 9, or in the range of pH 5.5 to 8.5, or in the range of pH 5.5 to 8, or in the range of pH 6 to 10, or in the range of pH 6 to 9, or in the range of pH 6 to 8.5, or in the range of pH 6 to 8.

For the process of dehydrating glucose to HMF, i.e. steps iv) a), IV) a) and C) a) the pH of the aqueous phase of the reaction medium may in particular be in the range of 1 to 9, such as a pH in the range of 1 to 8, or in the range of 1 to 7, or in the range of 1 to 6, or in the range of 1 to 5, or in the range of 1 to 4, or in the range of 1.5 to 8, or in the range of 1.5 to 7, or in the range of 1.5 to 6, or in the range of 1.5 to 5, or in the range of 1.5 to 4.

The dehydration of glucose and/or fructose and/or mannose to HMF mainly takes place in the aqueous phase of the reaction medium and the process may create by-products. Some of these by-products are acidic and they may therefore cause the pH of the aqueous phase to fall as the dehydration of glucose and/or fructose and/or mannose to HMF takes place. Thus in the context of the present invention the pH range of the aqueous phase of the reaction medium refers to $t_0$ of the dehydration process in steps i), iv) a), II), IV) a), A and C) b). Thus it is the pH of the aqueous phase of the reaction medium at the point in time where all components are present but prior to any actual dehydration of fructose or glucose or mannose to HMF has taken place. For example if the method of the present invention is run as continuous process on an industrial scale the pH of composition comprising fructose, glucose, mannose, fructose and glucose, or fructose and mannose, may be the same as the pH of the aqueous phase of the reaction medium at $t_0$ when no acidic catalysts are added to the reaction medium. For example if the starting material, i.e. the composition comprising fructose, fructose and mannose, or fructose and glucose, used for the dehydration of fructose to HMF, i.e. in steps i), y), II) and A) has been obtained from conversion of glucose to fructose, or mannose to fructose, by an enzymatic reaction catalyzed by a glucose isomerase or mannose isomerase, e.g. in steps —i), iv) b), x), I), IV) b) or C) b), the pH of the composition obtained from this conversion will typically be in the range of 6.5-7.5. As glucose isomerase currently is used on an industrial basis as columns to which the glucose isomerase is immobilized this means that the pH of the composition leaving the glucose isomerase may typically be in the range of 6.5-7.5. It may of course be possible to adjust the pH of this composition before it enters the dehydration process in steps i), y), II) or A).

In alternative embodiment the aqueous phase of the reaction medium for the process of dehydrating fructose to HMF; i.e. steps i), y), II) and A) does not contain an acidic catalyst or does not comprise a strong acid. In the context of the present invention "does not contain an acidic catalyst" means that no acidic catalyst has been added to the reaction medium. An "acidic catalyst" may in particular be an acid which has a $pK_a$-value below 5, such as a $pK_a$-value below 4, or a $pK_a$-value below 3, or a $pK_a$-value below 2, or have a $pK_a$-value between 1-5, such as between 1-4, or between 1-3 or between 1-2, or between 1-1.5, or between 2-4, such as between 2-3, or between 2.5-3.5; or between 1.5-4, such as between 1.5-3, or between 1.5-2.5; or between 3-5, such as between 3.5-4.5 or between 3-4, or between 4-5. An "acidic catalyst" may in particular be a "strong acid", wherein a strong acid is an acid with a $pK_a$-value below 1. The term "does not comprise a strong acid" means that no acids with a $pK_a$-value below 1 has been added to the reaction medium; i.e. "a strong acid" is in the context of the present invention to be understood as an acid with a $pK_a$-value which is lower than 1 ($pK_a$(strong acid)<1). It does not exclude the presence of acidic compounds which may be formed as by-products of the dehydration process. Examples of such acidic catalysts include but are not limited to mineral acids, such as HCl, $HNO_3$, $H_2SO_4$, $H_3PO_4$, sulfonic acid, sulfonic acid resins, zeolites, acid-functionalized Mobil composition materials (MCM's), sulphated zirconia, heteropolyacids, phosphates such as $NbOPO_4$, vanadium phosphate, solid silica- and silica-alumina, Brøndsted or Lewis acid catalyst. The inventors of the present invention has surprisingly found out that the salt present in the aqueous phase is able to function as catalyst for the dehydration of fructose to HMF making it unnecessary to use other catalysts such as acidic catalysts which have previously been used.

Hence in a particular embodiment the aqueous phase of the reaction medium in steps i), y), II) and A) of the present invention does not comprise an acidic catalyst or does not comprise a strong acid.

Although, the inventors of the present invention found out that it is not necessary to use an acidic catalyst for the dehydration of fructose to HMF such catalysts may still be present in the aqueous phase of the reaction for example in small amounts. Thus any of the above mentioned catalysts may be present in the aqueous phase of the reaction medium.

Furthermore, for the process of dehydration of glucose to HMF, or mannose to HMF, i.e. steps iv) a), IV) a) and C) a) it may also be an advantage to include an acidic catalyst, such as $AlCl_3$ to minimize the production of unwanted side-products. The optimal reaction conditions for the dehydration of fructose, mannose and glucose, respectively, to HMF are not the same.

The reaction medium also comprises an organic phase. The organic phase of the reaction medium comprises an organic solvent and optionally other components.

A suitable organic solvent is preferably a solvent which is non-miscible with the aqueous phase of the reaction medium and which is capable of solubilising HMF at room temperature (25° C.) or higher. More preferably the organic solvent is a solvent having a higher solubility for HMF than the solubility of HMF in the aqueous phase, so that HMF is extracted from the aqueous phase into the organic phase.

Thus the organic solvent and/or the organic phase may in particular be chosen so that the partition coefficient of the aqueous and organic phase with respect to HMF is at least 0.8, such as at least 0.9, or at least 1.0, or at least 1.1, or at least 1.2, or at least 1.3, or at least 1.4, or at least 1.5, such as at least 2, wherein the partition coefficient is determined at room temperature, e.g. between 20-25° C., i.e. at 20° C., 21° C., 22° C., 23° C., 24° C. or 25° C. and 1 atm (standard atmosphere pressure).

Examples of such organic solvents include in particular but are not limited to alcohols, ketones, chlorinated alkanes, ethers, acetates or combinations thereof.

In a particular embodiment the organic solvent may be methyl-isobutylketone (MIBK), tetrahydrofuran (THF), 2-BuOH (2-butanol) or any combination of two or more of these organic solvents. Combinations of the organic solvents may for example be MIBK and 2-BuOH, such as in a ratio of between 5:5 and 9:1 MIBK:2-BuOH, more particularly 7:3 MIBK:2-BuOH. THF is shown to be good at extracting HMF from the aqueous phase and the amount of unwanted side-products is also diminished compared to when other organic solvents are used. Other examples of useful organic solvents include but are not limited to low molecular weight alcohols, such as fusel oil, isoamyl alcohol, butanol or isopentyl alcohol, straight or branched alcohols, such as pentanol, tertbutyl alcohol or 1-butanol, straight or branced alkanones, such as butanone, pentanone, hexanone, heptanone, diisobutylketone, 3-methyl-2-butanone, or 5-methyl-3-heptanone, cycloalkanones, such as cyclobutanone, cylclopentanone or cyclohexanone. Other examples of organic solvents include but are not limited to nitriles, such as benzonitrile, aliphatic and cycloaliphatic ethers, such as dichloroethylether or dimethyl ether, saturated and unsaturated aliphatic or aromatic hydrocarbons, such as furan, or nitroalkanes, such as nitromethane or nitropropane, and halogenated alkanes, such as dichloromethane (DCM), chloromethane, trichloromethane or trichloroethane.

The ratio of the volume of the aqueous phase to the volume of the organic phase may in a particular embodiment be in the range of 1:0.1 to 1:100 (aqueous phase:organic phase or aq:org).

As described above it is an advantage if the solubility of HMF is larger in the organic phase than in the aqueous phase of the reaction medium. This may be described by a parameter called the partition coefficient of the aqueous and organic phase with respect to HMF. In a particular embodiment the partition coefficient for the aqueous and organic phase with respect to HMF is at least 0.8, such as at least 0.9, or at least 1.0, or at least 1.1, or at least 1.2, or at least 1.3, or at least 1.4, or at least 1.5, such as at least 2, wherein the partition coefficient is determined at room temperature, e.g. between 20-25° C., i.e. at 20° C., 21° C., 22° C., 23° C., 24° C. or 25° C. and 1 atm (standard atmosphere pressure).

EXAMPLES

In the following examples the HMF yield refers to the percentage of sugars that are converted to HMF; i.e. (mole of HMF/mole of sugars added to the reaction)×100%. The selectivity refers to the percentage of converted sugars which are converted to HMF; i.e. (mole of HMF/mole of converted sugars)×100% which can also be calculated as (% HMF yield/% converted sugars)×100%.

Example 1

Selective Dehydration of Fructose from Fructose/Glucose Mixture 2.5 mL of an aqueous solution of 171 g/L glucose, 123 g/L fructose, 245 g/L sodium chloride and 0.36 g/L hydrogen chloride was added 10 mL MIBK and stirred under a nitrogen atmosphere in a 25 mL sealed glass reactor tube at 140° C. for 1 hour. The organic and aqueous phases of the product were analyzed by HPLC (High Pressure Liquid Chromatography), showing that 49% of the introduced glucose or fructose was converted, leaving 87% of the introduced glucose unconverted. The yield of HMF was 33%, corresponding to a selectivity of 68%.

The HPLC conditions were as follows:
Instrument: Agilent 1200 (with vacuum degasser, Binary pump, Autosampler, Column heater, Multiple wavelength UV/VIS detector, Refractive index detector)
Column=Aminex HPX-87H (Biorad, Hercules, Calif.); 300× 7.8 mm+Guard column of same material
Flow=0.6 mL/min
Solvent=0.005 M $H_2SO_4$
Temp=60° C.
Analysis time=50 minutes Example 2

Dehydration of Glucose to HMF with Aluminum Chloride 2.5 mL of an aqueous solution of 245 g/L sodium chloride, 294 g/L glucose and 1.31 g/L aluminum chloride was added 10 mL MIBK and stirred under a nitrogen atmosphere in a 25 mL sealed glass reactor tube at 140° C. for 2.5 hours. The organic and aqueous phases of the product were analyzed by HPLC, showing that 85% of the glucose was converted. The yield of HMF was 51%, corresponding to a selectivity of 60%.

Example 3

Two Step Dehydration of Fructose/Glucose Mixture—with Solvent Exchange 2.5 mL of an aqueous solution of 245 g/L sodium chloride, 171 g/L glucose, 123 g/L fructose and 0.36 g/L hydrogen chloride was added 10 mL MIBK and stirred under a nitrogen atmosphere in a 25 mL sealed glass reactor tube at 140° C. for 1 hour. The reaction mixture was cooled and the organic phase was collected. To the aqueous phase was added 10 mL MIBK and 50 µL aqueous solution of 0.5M aluminum chloride. The mixture was stirred under a nitrogen atmosphere in a 25 mL sealed glass reactor tube at 140° C. for two to four hours. The aqueous and organic phases were analyzed by HPLC. The results are given in table 1.

TABLE 1

Results for two step dehydration of HFCS42 with solvent exchange

| Reaction time with $AlCl_3$ | Conversion of sugars | HMF yield | HMF selectivity |
| --- | --- | --- | --- |
| 2 hours | 70% | 51% | 72% |
| 4 hours | 90% | 63% | 70% |

Example 4

Two Step Dehydration of Fructose/Glucose Mixture—without Solvent Exchange 2.5 mL of an aqueous solution of 245 g/L sodium chloride, 171 g/L glucose, 123 g/L fructose and 0.36 g/L hydrogen chloride was added 10 mL MIBK and stirred under a nitrogen atmosphere in a 25 mL sealed glass reactor tube at 140° C. for 1 hour. The reaction mixture was cooled and 50 µL aqueous solution of 0.5M aluminum chloride was added. The mixture was stirred under a nitrogen atmosphere in a 25 mL sealed glass reactor tube at 140° C. for two to four hours. The aqueous and organic phases were analyzed by HPLC. The results are given in table 2.

TABLE 2

Results for two step dehydration of HFCS42 without solvent exchange

| Reaction time with $AlCl_3$ | Conversion of sugars | HMF yield | HMF selectivity |
| --- | --- | --- | --- |
| 2 hours | 72% | 50% | 70% |
| 4 hours | 86% | 51% | 59% |

Example 5

Synthesis and Extraction of HMF from Fructose at 160° C. in a Biphasic Water/MIBK Reactor with NaCl Addition 3 ml of aqueous sample phase solution containing 20% (wt/wt) fructose were poured into a 15 ml reactor. NaCl was added to the water phase to give a NaCl concentration of 50 g/L followed by addition of 12 ml MIBK as organic HMF extraction phase.

The reaction mixture was heated to 160° C. and run for 120 min, where after samples were taken for HPLC analysis.

The HMF yield was 75%, the selectivity 79% and fructose conversion 94%

Under the same conditions but without addition of NaCl the following results were obtained:

The HMF yield was 39%, the selectivity 86% and the fructose conversion 46%

Example 6

Synthesis and Extraction of HMF from Fructose at 160° C. in a Biphasic Water/MIBK Reactor with NaCl Addition 3 ml of aqueous sample phase solution containing 20% (wt/wt) fructose were poured into a 15 ml reactor. 0.2 g NaCl was added to the water phase.

5 mg of the sulfated zirconia catalyst were then added to the water phase reaction mixture followed by addition of 12 ml MIBK as organic HMF extraction phase. The reaction mixture was heated to 160° C. and run for 240 min, where after samples were taken for HPLC analysis.

The HMF yield was 68% and the selectivity 70%.

Example 7

Synthesis of HMF with Glucose/Fructose Mixture at 150° C.

An aqueous solution containing 10 wt % glucose and 10 wt % fructose (3 mL, 0.0022 mol glucose, 0.0023 mol fructose) was mounted in an Ace vial pressure tube (stable to ~20 Bar). Solid NaCl (150 mg, 0.0026 mol) was dissolved in the aqueous phase followed by the addition of MIBK (12 ml) as extracting solvent. The pressure stable tube was sealed and heated to 150° C. for 2 h and subsequently allowed cooling to room temperature. A sample of the reaction mixture was collected and filtered through a syringe filter (0.45 µm PTFE), mixed with an internal standard (i-PrOH) and analyzed via HPLC. The results of the HPLC showed 84% glucose from glucose, 0.0019 mol; 44% fructose from fructose, 0.0010 mol; 33% HMF from fructose, 0.0008 mol; total sugar conversion 33%; HMF selectivity from fructose 59%.

Example 8

Synthesis of HMF with Glucose/Fructose Mixture at 160° C.

An aqueous solution containing 10 wt % glucose and 10 wt % fructose (3 mL, 0.0022 mol glucose, 0.0023 mol fructose) was mounted in an Ace vial pressure tube (stable to ~20 Bar). Solid NaCl (150 mg, 0.0026 mol) was dissolved in the aqueous phase followed by the addition of MIBK (12 ml) as extracting solvent. The pressure stable tube was sealed and heated to 160° C. for 105 min and subsequently allowed cooling to room temperature. A sample of the reaction mixture was collected and filtered through a syringe filter (0.45 µm PTFE), mixed with an internal standard (i-PrOH) and analyzed via HPLC. The results of the HPLC showed 80% glucose from glucose, 0.0018 mol; 4% fructose from fructose, $9.5 \cdot 10^{-5}$ mol; 64% HMF from fructose, 0.0015 mol; total sugar conversion 59%; HMF selectivity from fructose 67%.

Example 9

Synthesis of HMF with Glucose at 150° C. (Control)

An aqueous solution containing 10 wt % glucose (3 mL, 0.0022 mol) was mounted in an Ace vial pressure tube (stable to ~20 Bar). Solid NaCl (150 mg, 0.0026 mol) was dissolved in the aqueous phase followed by the addition of MIBK (12 ml) as extracting solvent. The pressure stable tube was sealed and heated to 150° C. for 2 h and subsequently allowed cooling to room temperature. A sample of the reaction mixture was collected and filtered through a syringe filter (0.45 µm PTFE), mixed with an internal standard (i-PrOH) and analyzed via HPLC. The results of the HPLC showed 95-97% glucose, 0.0021-0.0022 mol; 2% HMF, $4.5 \cdot 10^{-5}$ mol; total sugar conversion 3-5%.

Example 10

Synthesis of HMF with Fructose at 150° C. (Control)

An aqueous solution containing 10 wt % fructose (3 mL, 0.0019 mol) was mounted in an Ace vial pressure tube (stable to ~20 Bar). Solid NaCl (150 mg, 0.0026 mol) was dissolved in the aqueous phase followed by the addition of MIBK (12 ml) as extracting solvent. The pressure stable tube was sealed and heated to 150° C. for 2 h and subsequently allowed cooling to room temperature. A sample of the reaction mixture was collected and filtered through a syringe filter (0.45 µm PTFE), mixed with an internal standard (i-PrOH) and analyzed via HPLC. The results of the HPLC showed 61% fructose, 0.0012 mol; 29% HMF, 0.005 mol; total sugar conversion 39%; HMF selectivity from fructose 73%.

Anticipations and Approximations for the Glucose/Fructose Mixture

The yield of glucose and fructose were calculated according to the initial amount of each present in the sample. Hereby the interconversion of glucose and fructose were neglected. The HMF yield was calculated based on the fructose only. Thereby a small amount arising from glucose was neglected. The amounts of formic acid and levulinic acid were below the detection limit of the HPLC apparatus. Please note that the conversions of fructose and glucose separately do not add up to the total sugar conversion as e.g. 100% fructose conversion≈50% total sugar conversion. HMF selectivity's were calculated based on the fructose conversion, due to the assumption above. The remaining products to complete the mass balance were not detected, but were likely to comprise of soluble and insoluble, reversible and irreversible dimers, trimers and polymers of glucose, fructose, HMF and combinations hereof.

Example 11

The Effect of Various Salts

Figure 2:
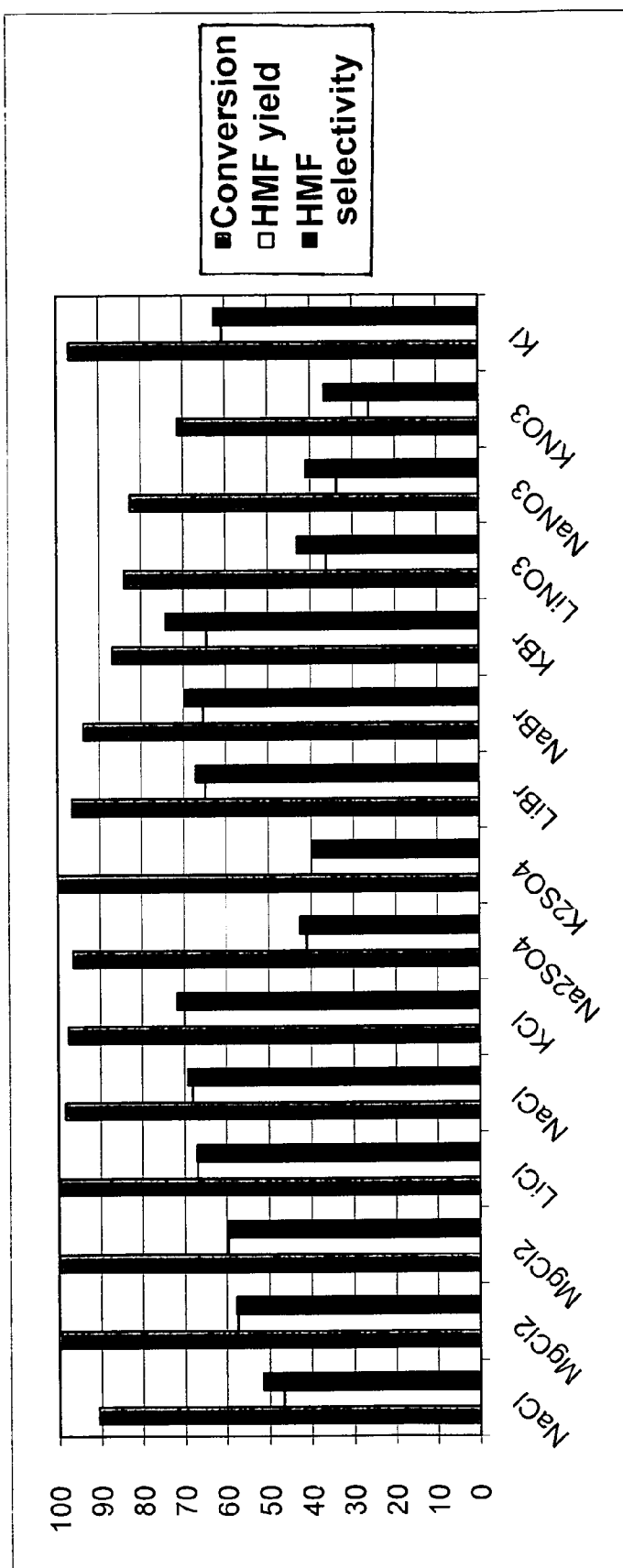
FIG. 2 shows the effect the choice of salt in the aqueous phase of the reaction medium has on the conversion of sugars, the HMF yield and the HMF selectivity all expressed as percentages. This figure is an illustration of some of the data obtained in example 11.

Generally, aqueous solutions containing 30 wt % fructose (3 mL, 0.0058 mol) were mounted in an Ace vial pressure tube (stable to ~20 Bar). Various solid salts (0.0026 mol) were dissolved in the aqueous phase followed by the addition of MIBK (12 ml) as extracting solvent. The pressure stable tube was sealed and heated to 160° C. for 2 h and subsequently allowed cooling to room temperature. A sample of the reaction mixture was collected and filtered through a syringe filter (0.45 µm PTFE), mixed with an internal standard (i-PrOH) and analyzed via HPLC. The results are shown below in table 3 and in FIG. 2.

The best result with respect to HMF yield was obtained with KCl (98% fructose conversion, 70% HMF yield, HMF selectivity 72%). The best result with respect to HMF selectivity was obtained with KBr (87% fructose conversion, 64% HMF yield, HMF selectivity 74%).

TABLE 3

| Salt | NaCl | MgCl$_2$ | MgCl$_2$ | LiCl | NaCl | KCl | Na$_2$SO$_4$ |
|---|---|---|---|---|---|---|---|
| Conversion | 90.7 | 99.5 | 99.9 | 99.7 | 98.3 | 97.6 | 96.5 |
| HMF yield | 46.7 | 57.5 | 59.6 | 66.9 | 68.1 | 70.0 | 41.1 |
| Selectivity | 51.5 | 57.8 | 59.7 | 67.1 | 69.2 | 71.7 | 42.6 |
| Mg | 150 | 522 | 261 | 109 | 150 | 191 | 365 |

| Salt | K$_2$SO$_4$ | LiBr | NaBr | KBr | LiNO$_3$ | NaNO$_3$ | KNO$_3$ | KI |
|---|---|---|---|---|---|---|---|---|
| Conversion | 100.0 | 96.6 | 93.9 | 86.9 | 84.0 | 82.6 | 71.3 | 97.0 |
| HMF yield | 39.9 | 64.8 | 65.3 | 64.4 | 36.2 | 33.8 | 26.1 | 60.5 |
| Selectivity | 39.9 | 67.1 | 69.5 | 74.1 | 43.1 | 40.9 | 36.6 | 62.4 |
| Mg | 447 | 223 | 264 | 305 | 177 | 218 | 260 | 426 |

Salts Investigated

MgCl$_2$ with respect to the Mg content, MgCl$_2$ with respect to the chloride content, NaCl, LiCl, KCl, Na$_2$SO$_4$ with respect to the sulphate content, K$_2$SO$_4$ with respect to the sulphate content, LiBr, NaBr, KBr, LiNO$_3$, NaNO$_3$, KNO$_3$, KI.

Example 12

Glucose Isomerase Performance at High Salt Concentrations

Standard Procedure for all Columns:

3 gram immobilized glucose isomerase (Sweetzyme™) was loaded in a lab-scale column heated to 60° C. and a substrate flow of 50 gram/hour was applied. The substrate was either normal 45 w/w % sterile filtered glucose solution containing 1 g/L MgSO$_4$.7H$_2$O and 0.18 g/L NaS$_2$O$_5$ or a modified 45 w/w % glucose syrup to which a relative high concentration of a salt was added after the indicated points in time. Samples were collected on a regular basis for HPLC analysis and the enzyme activity was calculated according to the following equation (Jorgensen, O. B., et al., Starch-Starke, 1988. 40(8), 307-313):

$$A = 0.926 \frac{F_w}{w} X_e \frac{DP_1}{100} DSln \frac{X_e - X_i}{X_e - X}$$

where:
A: specific activity of immobilized enzyme (micromol/min/g enzyme) (IGIU/g: Immobilized Glucose Isomerase Units/g)
0.926: unit conversion factor
$F_w$: Flow rate of syrup (g/h)
w: Weight of enzyme (g)
$DP_1$: Inlet % of (glucose+fructose) in dry substance (100 at analytical conditions)
DS: Dry substance content (%)
X: Conversion=outlet % fructose/$DP_1$
$X_i$: inlet % fructose/$DP_1$
$X_e$: X at equilibrium (0.51 at 60° C.)
$DP_1$, $X_i$ and $X_e$ were assumed constant with following values:
$DP_1$: 99.7
$X_i$: 0
$X_e$: 0.5078

Figure 3:
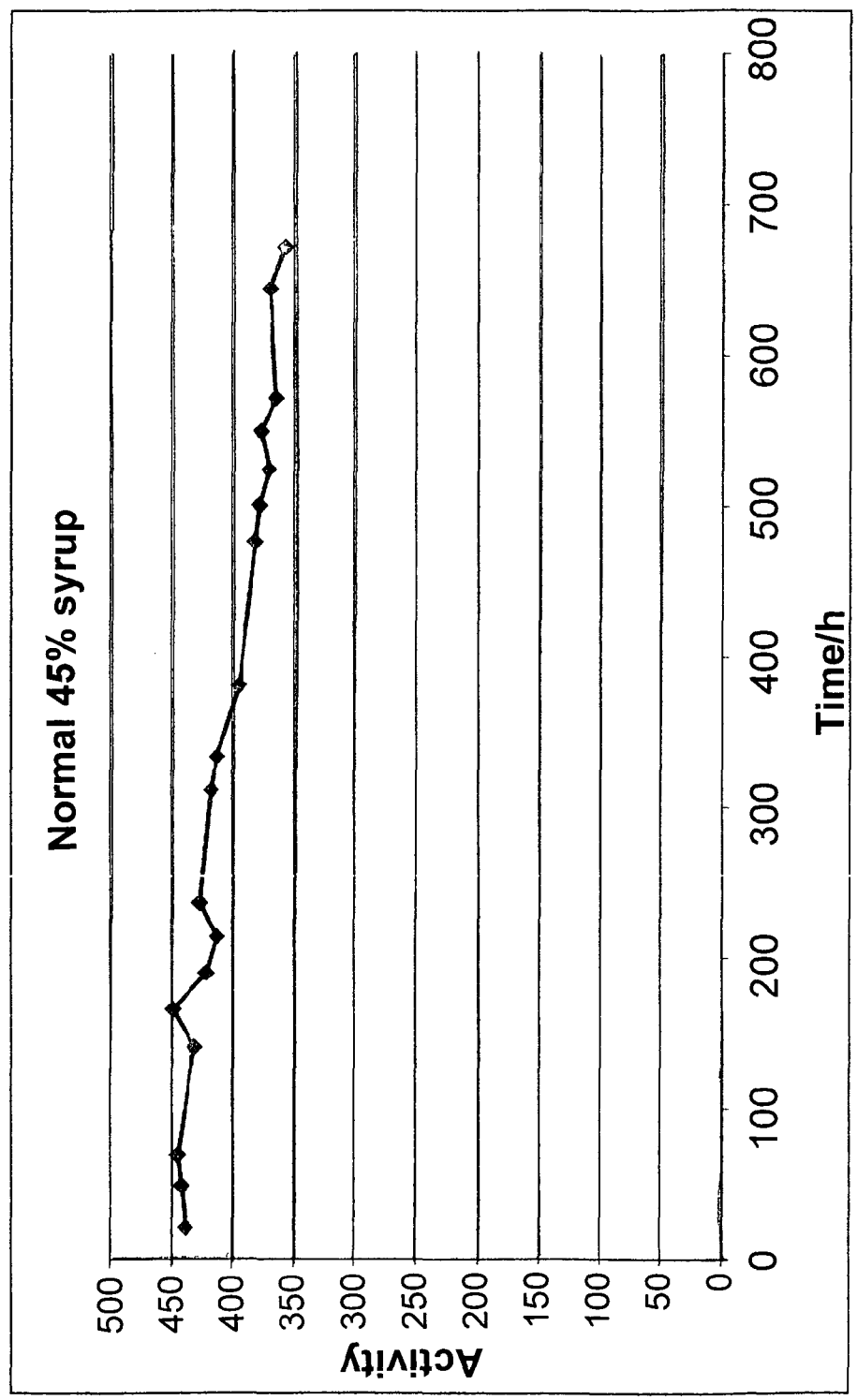
FIG. 3 shows the activity of immobilized glucose isomerase (Sweetzyme™) as a function of time with a standard substrate containing 45 w/w % glucose syrup. This figure is an illustration of some of the data obtained in example 12.

The following salt conditions were applied for 6 columns
Column 1:

Normal 45 w/w % sterile filtered glucose solution containing 1 g/L MgSO$_4$.7H$_2$O and 0.18 g/L NaS$_2$O$_5$. Key performance results are presented in table 4 and activity results are listed in table 5 and FIG. 3 shows a graphical presentation of the course of the activity.

Figure 4:
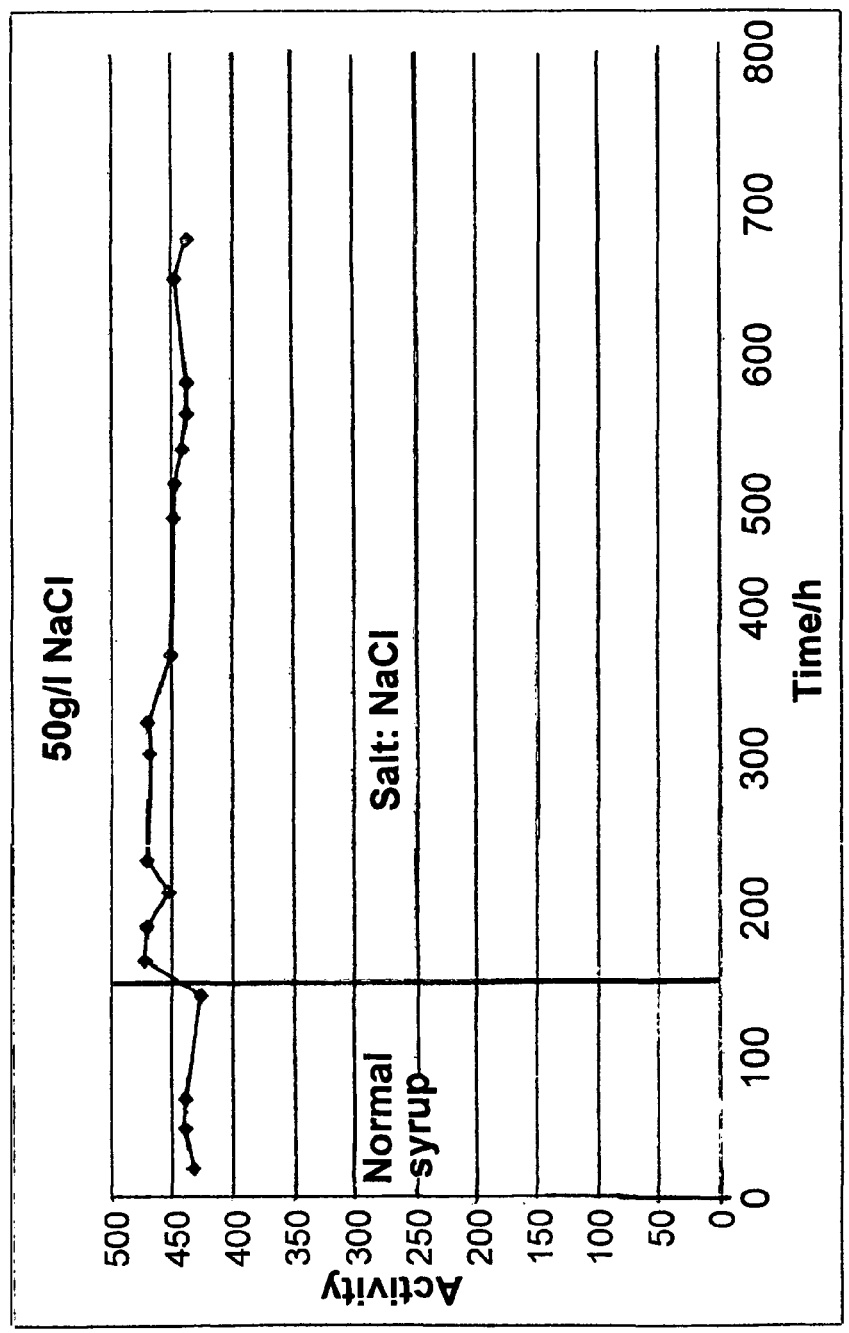
FIG. 4 shows the activity of immobilized glucose isomerase (Sweetzyme™) as a function of time with a modified 45 w/w % glucose syrup substrate containing a high concentration of NaCl. This figure is an illustration of some of the data obtained in example 12.

Column 2:

Sodium chloride (NaCl) mixed in standard 45% glucose syrup (as in column 1) to give a final concentration of NaCl of 50 g/l or 0.86M. Key performance results are presented in table 4 and activity results are listed in table 5 and FIG. 4 shows a graphical presentation of the course of the activity.

Figure 5:
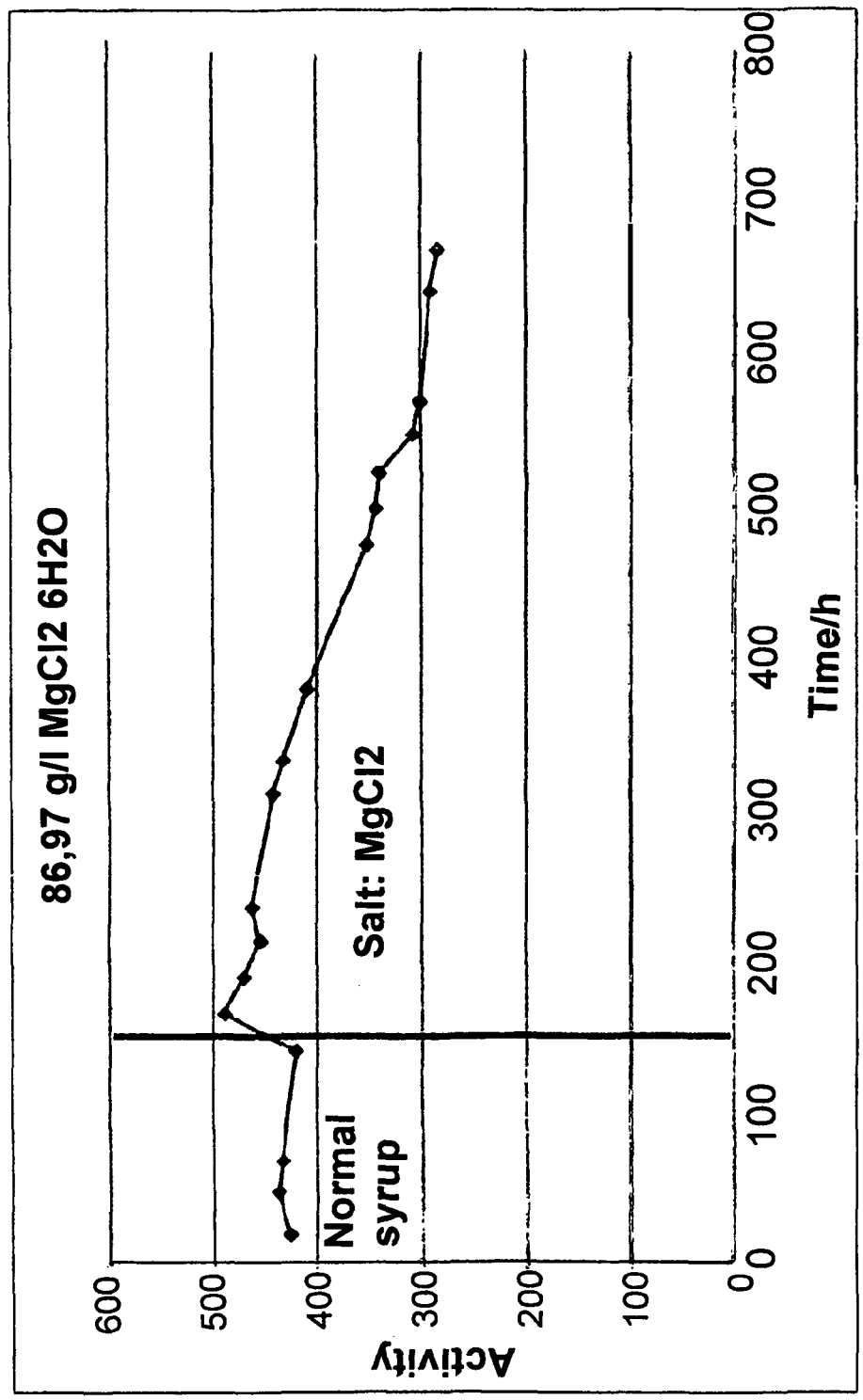
FIG. 5 shows the activity of immobilized glucose isomerase (Sweetzyme™) as a function of time with a modified 45 w/w % glucose syrup substrate containing a high concentration of $MgCl_2$, $6H_2O$. This figure is an illustration of some of the data obtained in example 12.

Column 3:

Magnesium chloride hexahydrate (MgCl$_2$.6H$_2$O) mixed in standard 45% glucose syrup (as in column 1) to give a final concentration of MgCl$_2$ 40.9 g/l or 0.86M with respect to chloride (86.97 g/l MgCl$_2$.6H$_2$O). Key performance results are presented in table 4 and activity results are listed in table 5 and FIG. 5 shows a graphical presentation of the course of the activity.

Figure 6:
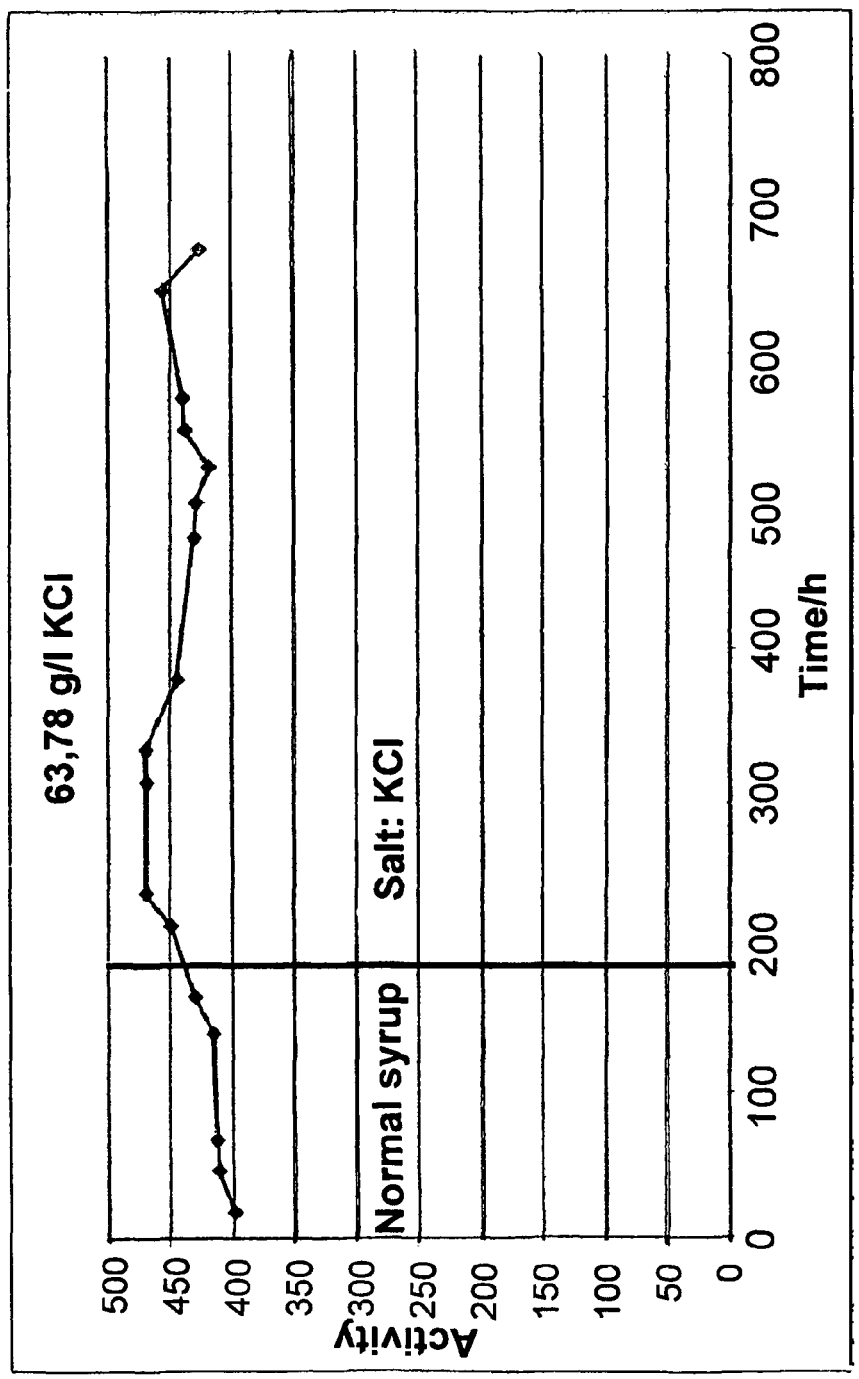
FIG. 6 shows the activity of immobilized glucose isomerase (Sweetzyme™) as a function of time with a modified 45 w/w % glucose syrup substrate containing a high concentration of KCl. This figure is an illustration of some of the data obtained in example 12.

Column 4:

Potassium chloride (KCl) mixed in standard 45% glucose syrup (as in column 1) to give a final concentration of KCl of 63.78 g/l or 0.86M. Key performance results are presented in table 4 and activity results are listed in table 5 and FIG. 6 shows a graphical presentation of the course of the activity.

Figure 7:
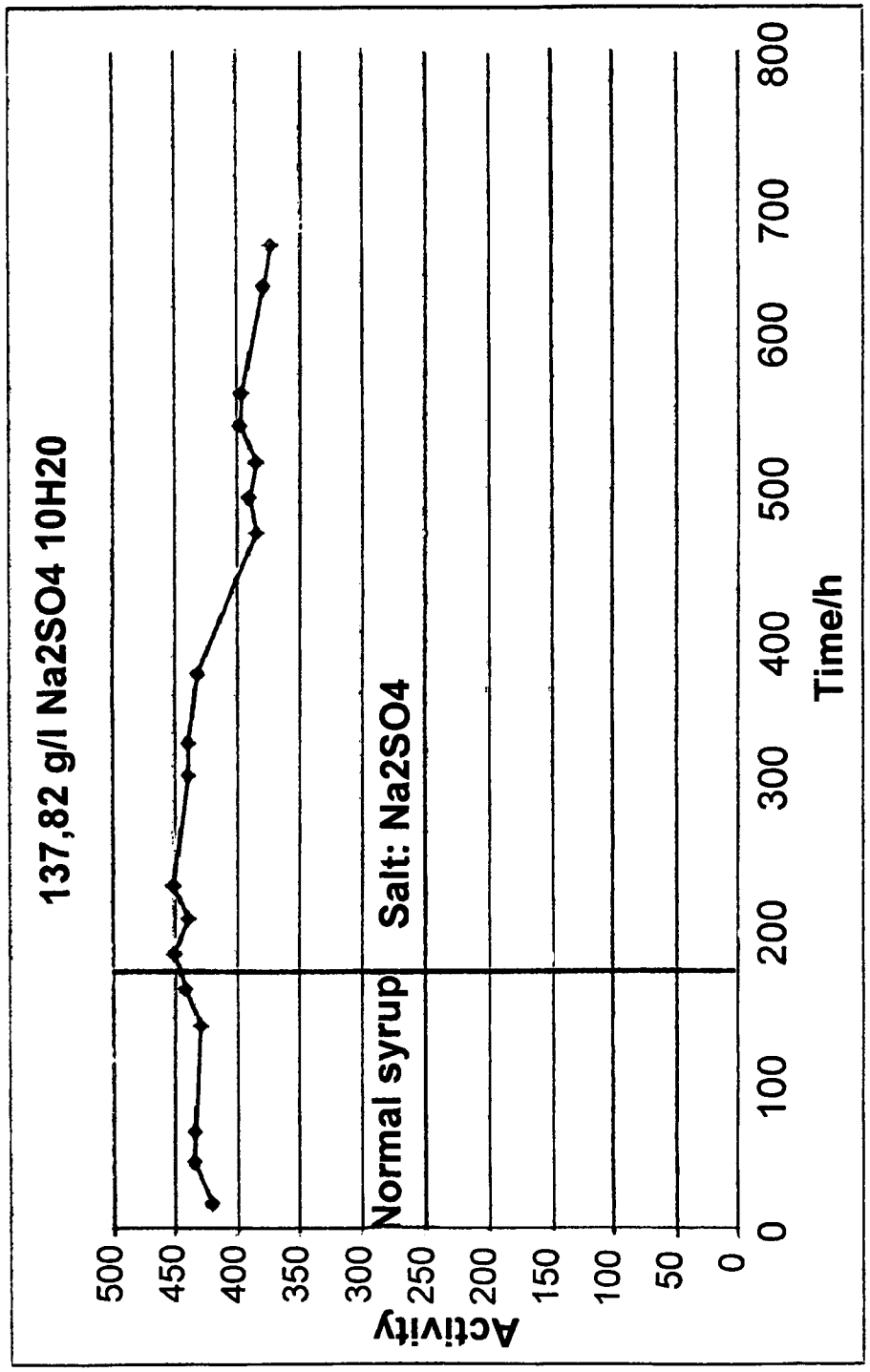
FIG. 7 shows the activity of immobilized glucose isomerase (Sweetzyme™) as a function of time with a modified 45 w/w % glucose syrup substrate containing a high concentration of $Na_2SO_4$, 10 $H_2O$. This figure is an illustration of some of the data obtained in example 12.

Column 5:

Sodium sulfate decahydrate (Na$_2$SO$_4$.10H$_2$O) mixed in standard 45% glucose syrup (as in column 1) to give a final concentration of Na$_2$SO$_4$ 61.08 g/l or 0.86M with respect to sodium (137.82 g/l Na$_2$SO$_4$.10H$_2$O). Key performance results are presented in table 4 and activity results are listed in table 5 and FIG. 7 shows a graphical presentation of the course of the activity.

Figure 8:
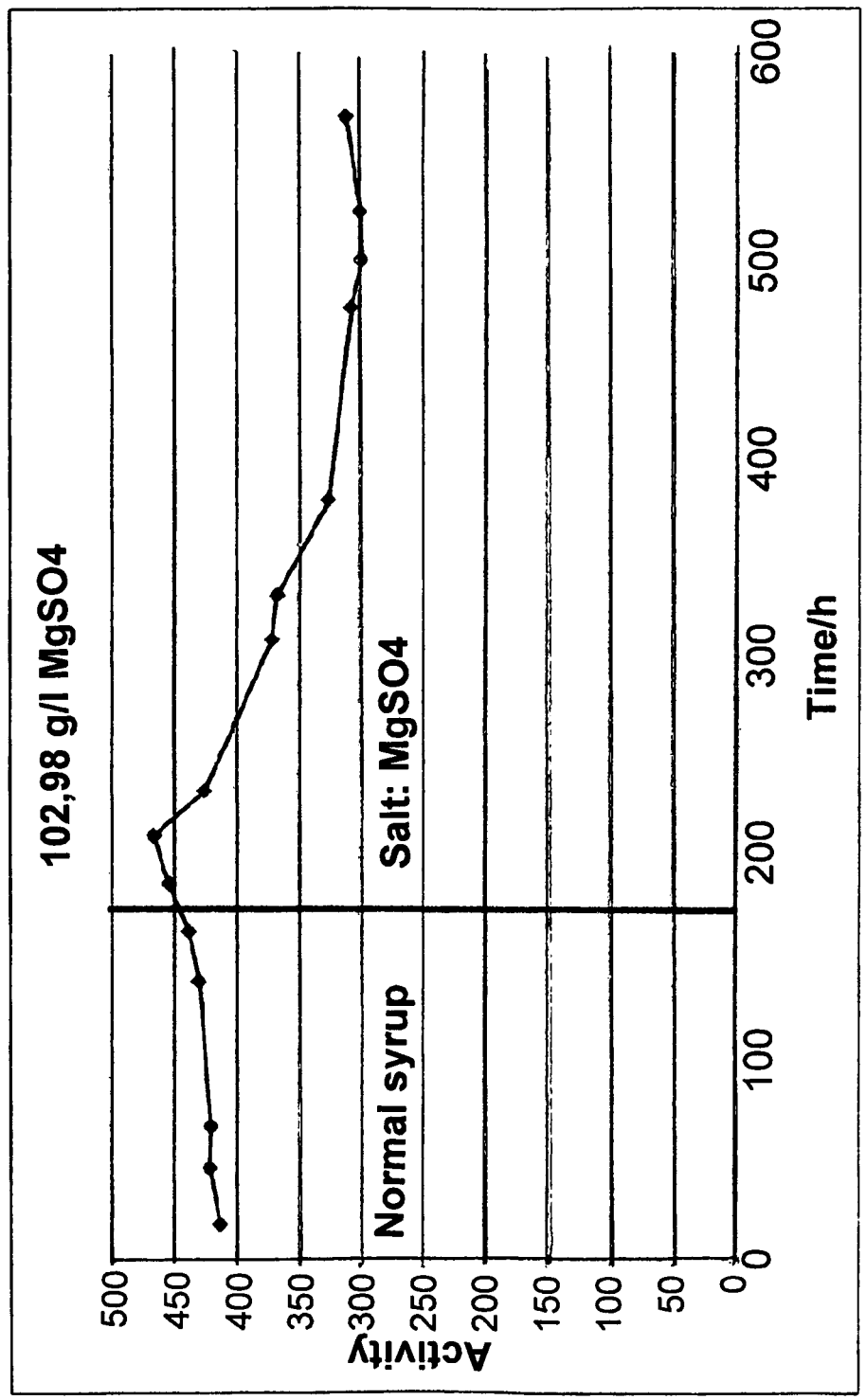
FIG. 8 shows the activity of immobilized glucose isomerase (Sweetzyme™) as a function of time with a modified 45 w/w % glucose syrup substrate containing a high concentration of $MgSO_4$. This figure is an illustration of some of the data obtained in example 12.

Column 6:

Magnesium sulfate (MgSO$_4$) mixed in standard 45% glucose syrup (as in column 1) to give a final concentration of MgSO$_4$ of 102.98 g/l or 0.86M. Key performance results are presented in table 4 and activity results are listed in table 5 and FIG. 8 shows a graphical presentation of the course of the activity.

TABLE 4

Key performance results for columns 1-6

| Column | Salt | Concentration (g/l) | Initial activity (IGIU/g) | Decay rate (IGIU/g/hr) |
|---|---|---|---|---|
| 1 | No | — | 438.60 | 0.10 |
| 2 | NaCl | 50.00 | 423.56 | 0.06 |
| 3 | $MgCl_2$ | 40.90 | 480.68 | 0.37 |
| 4 | KCl | 63.78 | 429.32 | 0.10 |
| 5 | $Na_2SO_4$ | 61.08 | 409.18 | 0.12 |
| 6 | $MgSO_4$ | 102.98 | 401.39 | 0.34 |

In conclusion, Sweetzyme™ shows good stability in the presence of NaCl, KCl and $Na_2SO_4$.

TABLE 5

Performance in terms of activity results for glucose isomerase for the six columns. Underlined numbers represent high salt conditions whereas no underlined numbers means normal syrup.

| Time/h | Activity | Time/h | Activity | Time/h | Activity |
|---|---|---|---|---|---|
| Column 1: normal syrup | | Column 2: 50 g/l NaCl | | Column 3: 40.9 g/l $MgCl_2$ | |
| 21.25 | 437.91 | 19.25 | 431.74 | 18.67 | 426.24 |
| 49.25 | 441.63 | 47.25 | 438.80 | 46.67 | 437.70 |
| 69.75 | 444.75 | 67.75 | 438.50 | 67.17 | 433.67 |
| 141.75 | 431.05 | 139.75 | 425.49 | 139.17 | 420.99 |
| 166.58 | 448.13 | _164.58_ | _471.33_ | _164.00_ | _489.74_ |
| 190.58 | 421.40 | _188.58_ | _469.46_ | _188.00_ | _471.38_ |
| 214.58 | 412.38 | _212.58_ | _451.52_ | _212.00_ | _454.69_ |
| 236.92 | 426.67 | _234.92_ | _468.84_ | _234.33_ | _463.15_ |
| 312.33 | 417.07 | _310.33_ | _466.38_ | _309.75_ | _442.52_ |
| 334.50 | 412.78 | _332.50_ | _468.14_ | _331.92_ | _432.66_ |
| 381.92 | 394.46 | _379.92_ | _449.12_ | _379.33_ | _409.54_ |
| 477.50 | 381.64 | _475.50_ | _446.72_ | _474.92_ | _351.70_ |
| 501.42 | 377.86 | _499.42_ | _445.83_ | _498.83_ | _343.55_ |
| 525.33 | 370.29 | _523.33_ | _439.69_ | _522.75_ | _340.36_ |
| 550.42 | 376.77 | _548.42_ | _436.34_ | _547.83_ | _307.44_ |
| 572.25 | 364.64 | _570.25_ | _436.11_ | _569.67_ | _301.06_ |
| 645.00 | 369.22 | _643.00_ | _446.01_ | _642.42_ | a) _291.22_ |
| 672.75 | 357.03 | _670.75_ | _435.86_ | _670.17_ | _283.93_ |
| Column 4: 63.78 g/l KCl | | Column 5: 61.08 g/l $Na_2SO_4$ | | Column 6: 102.98 g/l $MgSO_4$ | |
| 18.17 | 398.12 | 17.83 | 418.97 | 17.50 | 412.41 |
| 46.17 | 410.62 | 45.83 | 433.23 | 45.50 | 420.62 |
| 66.67 | 411.97 | 66.33 | 432.90 | 66.00 | 419.46 |
| 138.67 | 415.42 | 138.33 | 427.76 | 138.00 | 428.95 |
| 163.50 | 429.63 | 163.17 | 439.97 | 162.83 | 436.79 |
| _211.50_ | _448.90_ | _187.17_ | _449.17_ | _186.83_ | _452.92_ |
| _233.83_ | _469.08_ | _211.17_ | _437.81_ | _210.83_ | _465.04_ |
| _309.25_ | _468.47_ | _233.50_ | _449.65_ | _233.17_ | _424.51_ |
| _331.42_ | _469.21_ | _308.92_ | _437.45_ | _308.58_ | _370.47_ |
| _378.83_ | _443.80_ | _331.08_ | _437.38_ | _330.75_ | _366.35_ |
| _474.42_ | _430.17_ | _378.50_ | _429.47_ | _378.17_ | _324.95_ |
| _498.33_ | _428.76_ | _474.08_ | _381.79_ | _473.75_ | _306.53_ |
| _522.25_ | _418.17_ | _498.00_ | _387.83_ | _497.67_ | _298.41_ |
| _547.33_ | _437.40_ | _521.92_ | _382.13_ | _521.58_ | _299.60_ |
| _569.17_ | _438.97_ | _547.00_ | _394.91_ | _568.50_ | _310.87_ |
| b) _641.92_ | _455.49_ | c) _568.83_ | _393.80_ | | |
| _669.67_ | _426.01_ | d) _641.58_ | _376.25_ | | |
| | | e) _669.33_ | _370.35_ | | |

Example 13

The effect of HMF on the Initial Activity of Sweetzyme™

To demonstrate the effect of 5-hydroxymethylfurfural (HMF) on the initial activity of Sweetzyme™ a number of batch experiments with varying amount of HMF were performed.

Standard Procedure:

2.5 gram immobilized glucose isomerase (Sweetzyme™) was loaded to a 250 mL square shaped bottles with screw cap. The bottles were placed in an orbital shaker and heated to 60° C. The substrate was either normal 45 w/w % sterile filtered glucose solution containing 1 g/L $MgSO_4.7H_2O$ and 0.18 g/L $NaS_2O_5$ or a modified 45 w/w % glucose syrup with addition of HMF. Samples were collected on a regular basis for HPLC analysis and the enzyme activity was calculated.

The following conditions were applied for 4 bottles. The term conversion is defined as the fructose/glucose ratio.

Figure 9:
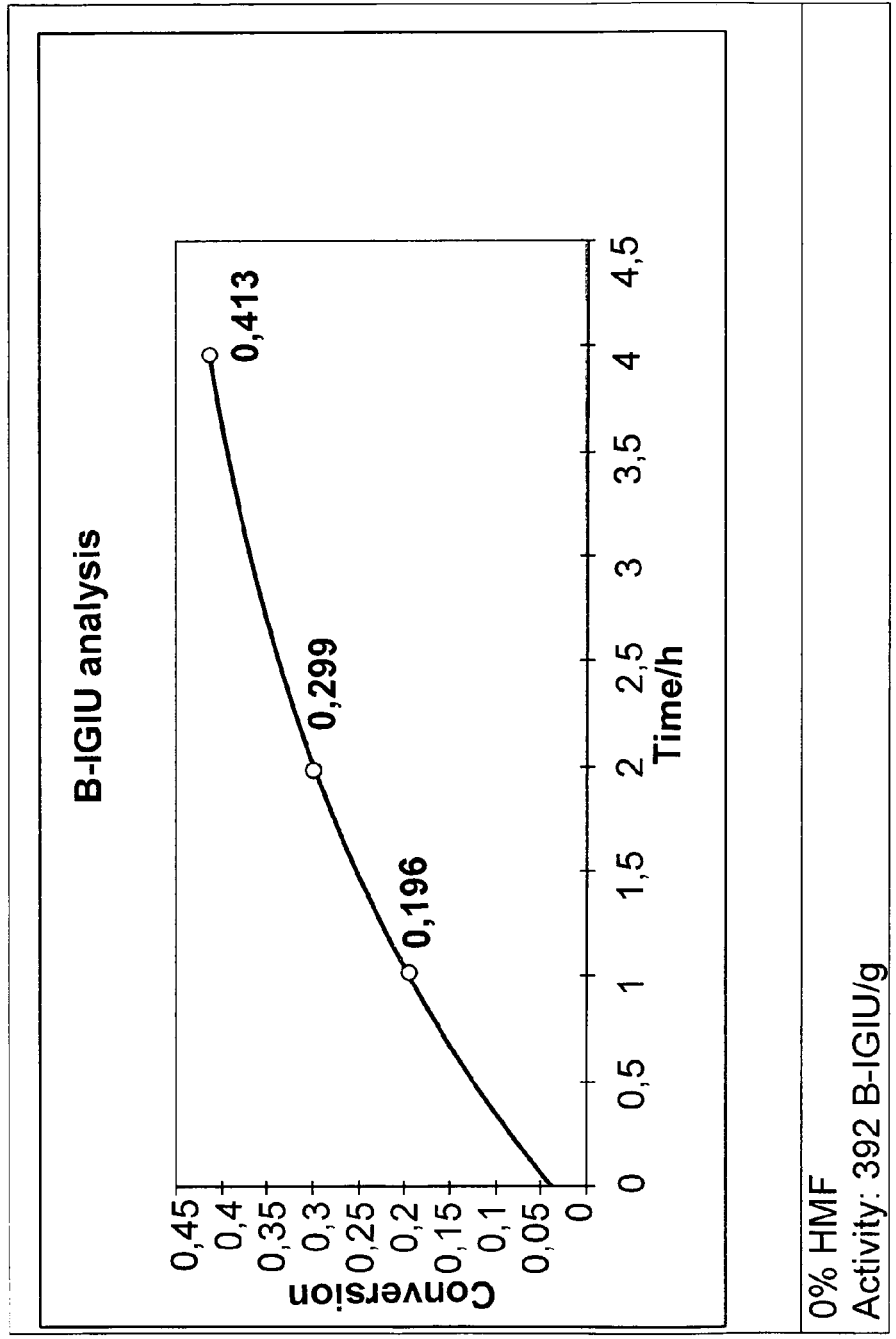
FIG. 9 shows the conversion of glucose to fructose by glucose isomerase (Sweetzyme™) as a function of time with a standard 45 w/w % glucose syrup substrate. This figure is an illustration of some of the data obtained in example 13.

Bottle 1:

Normal 45 w/w % sterile filtered glucose solution containing 1 g/L $MgSO_4.7H_2O$ and 0.18 g/L $NaS_2O_5$. Conversion vs. time is presented in FIG. 9 and the initial activity is calculated to be 392.

Figure 10:
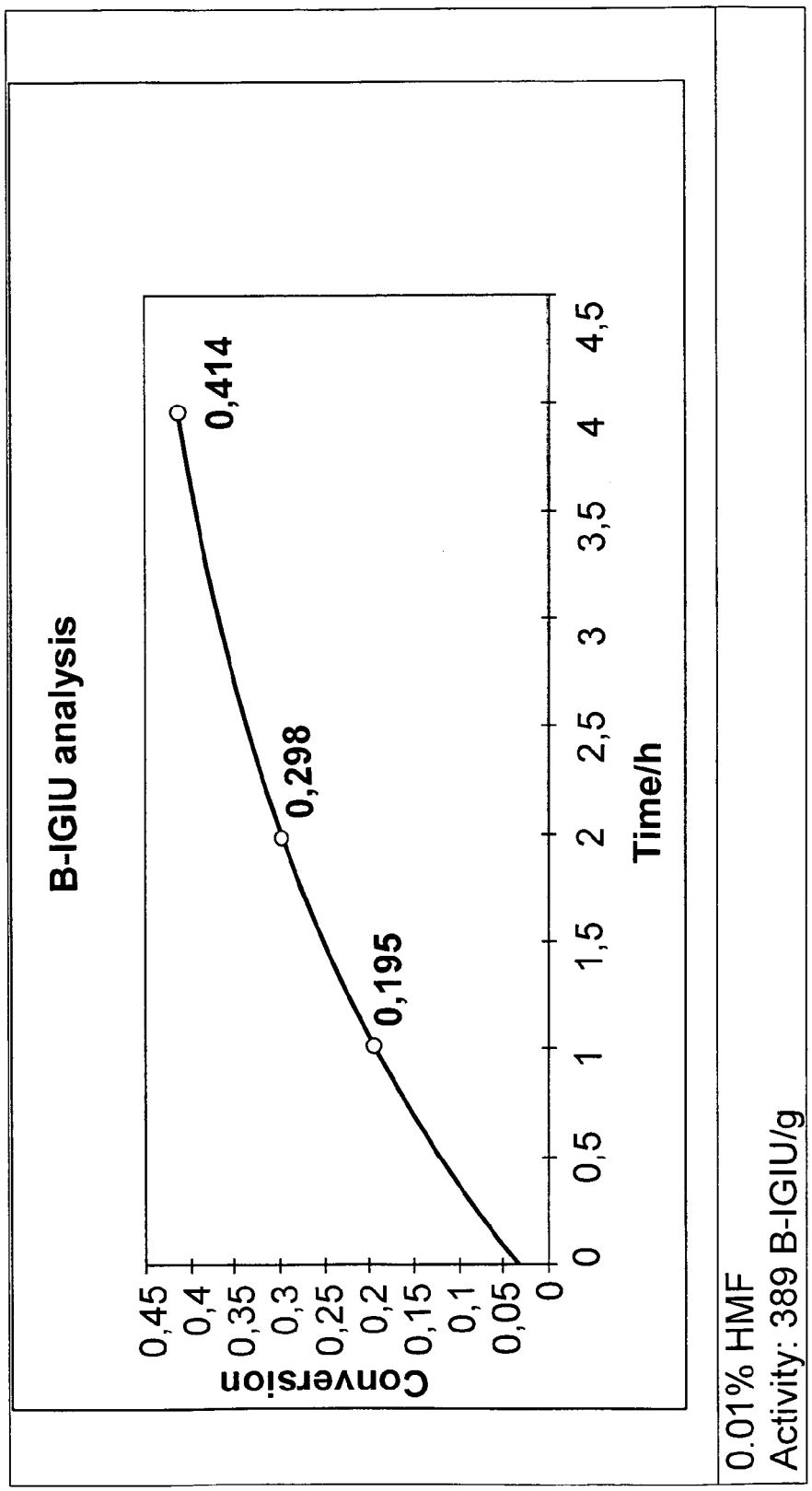
FIG. 10 shows the conversion of glucose to fructose by glucose isomerase (Sweetzyme™) as a function of time with a modified 45 w/w % glucose syrup substrate containing 0.01% HMF. This figure is an illustration of some of the data obtained in example 13.

Bottle 2:

HMF is mixed in standard 45% glucose syrup (as in bottle 1) to give a final concentration of HMF of 0.01 w/w %. Conversion vs. time is presented in FIG. 10 and the initial activity is calculated to be 389.

Figure 11:
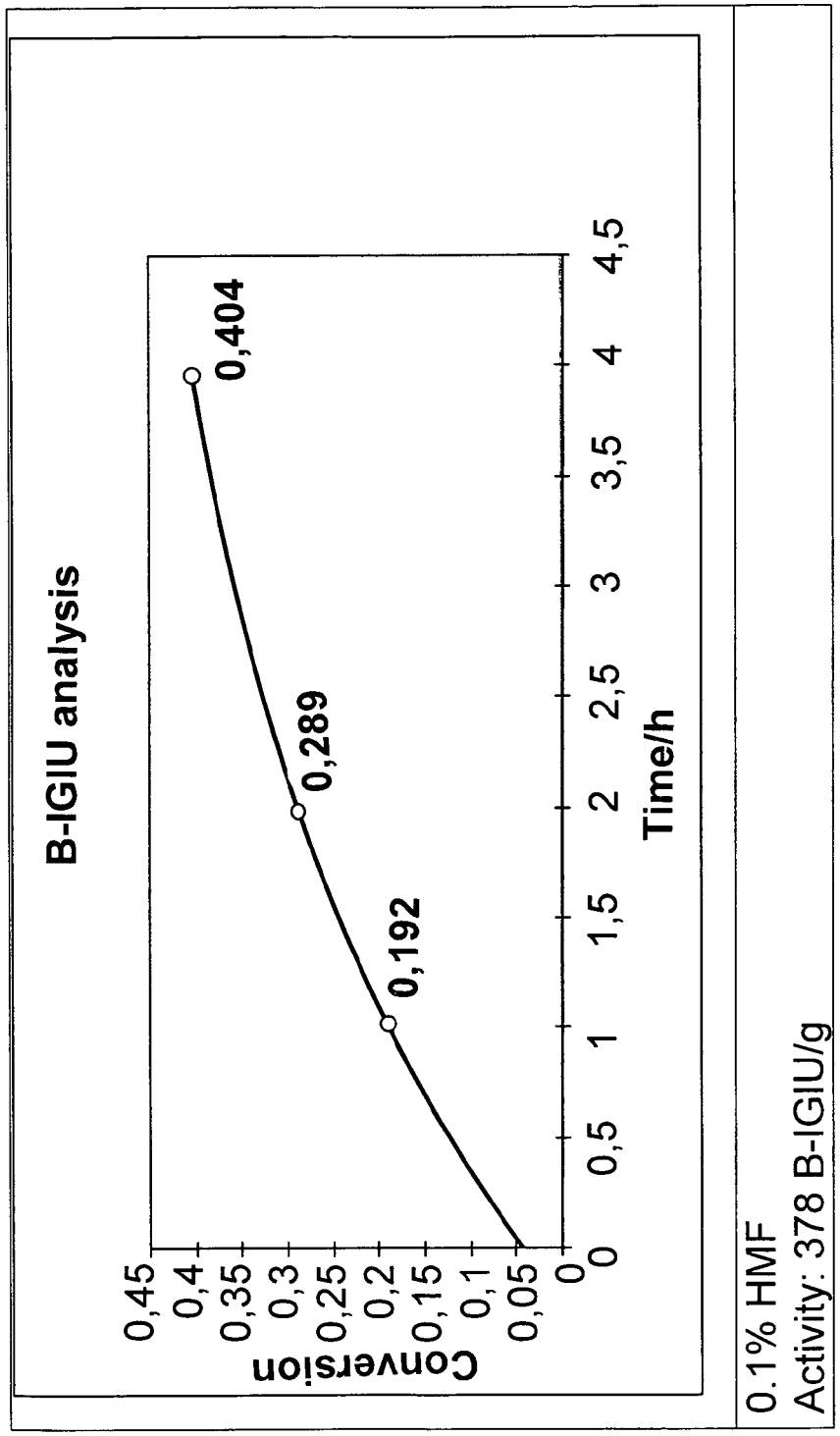
FIG. 11 shows the conversion of glucose to fructose by glucose isomerase (Sweetzyme™) as a function of time with a modified 45 w/w % glucose syrup substrate containing 0.1% HMF. This figure is an illustration of some of the data obtained in example 13.

Bottle 3:

HMF is mixed in standard 45% glucose syrup (as in bottle 1) to give a final concentration of HMF of 0.1 w/w %. Conversion vs. time is presented in FIG. 11 and the initial activity is calculated to be 378.

Figure 12:
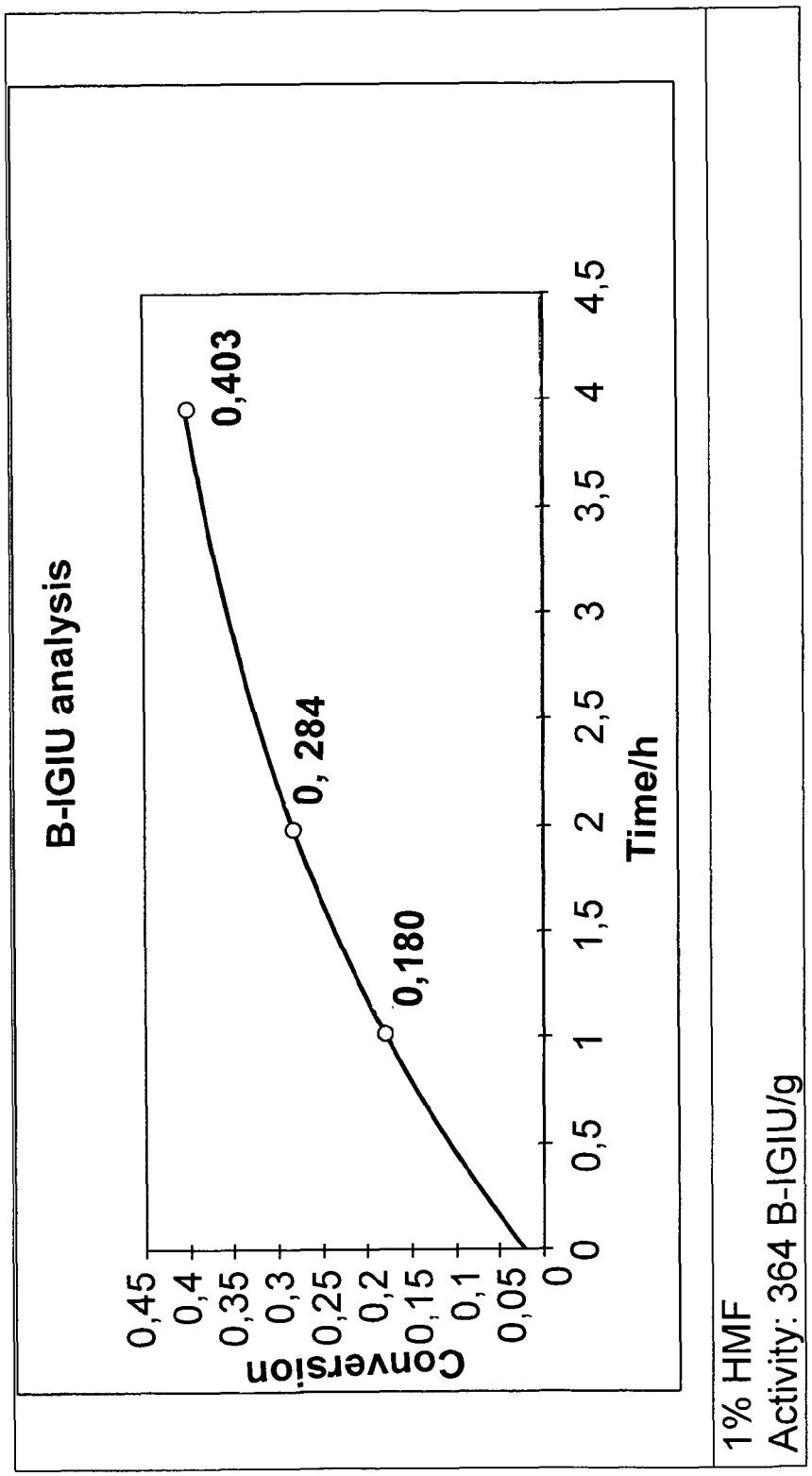
FIG. 12 shows the conversion of glucose to fructose by glucose isomerase (Sweetzyme™) as a function of time with a modified 45 w/w % glucose syrup substrate containing 1% HMF. This figure is an illustration of some of the data obtained in example 13.

Bottle 4:

HMF is mixed in standard 45% glucose syrup (as in bottle 1) to give a final concentration of HMF of 1 w/w %. Conversion vs. time is presented in FIG. 12 and the initial activity is calculated to be 364.

Figure 13:
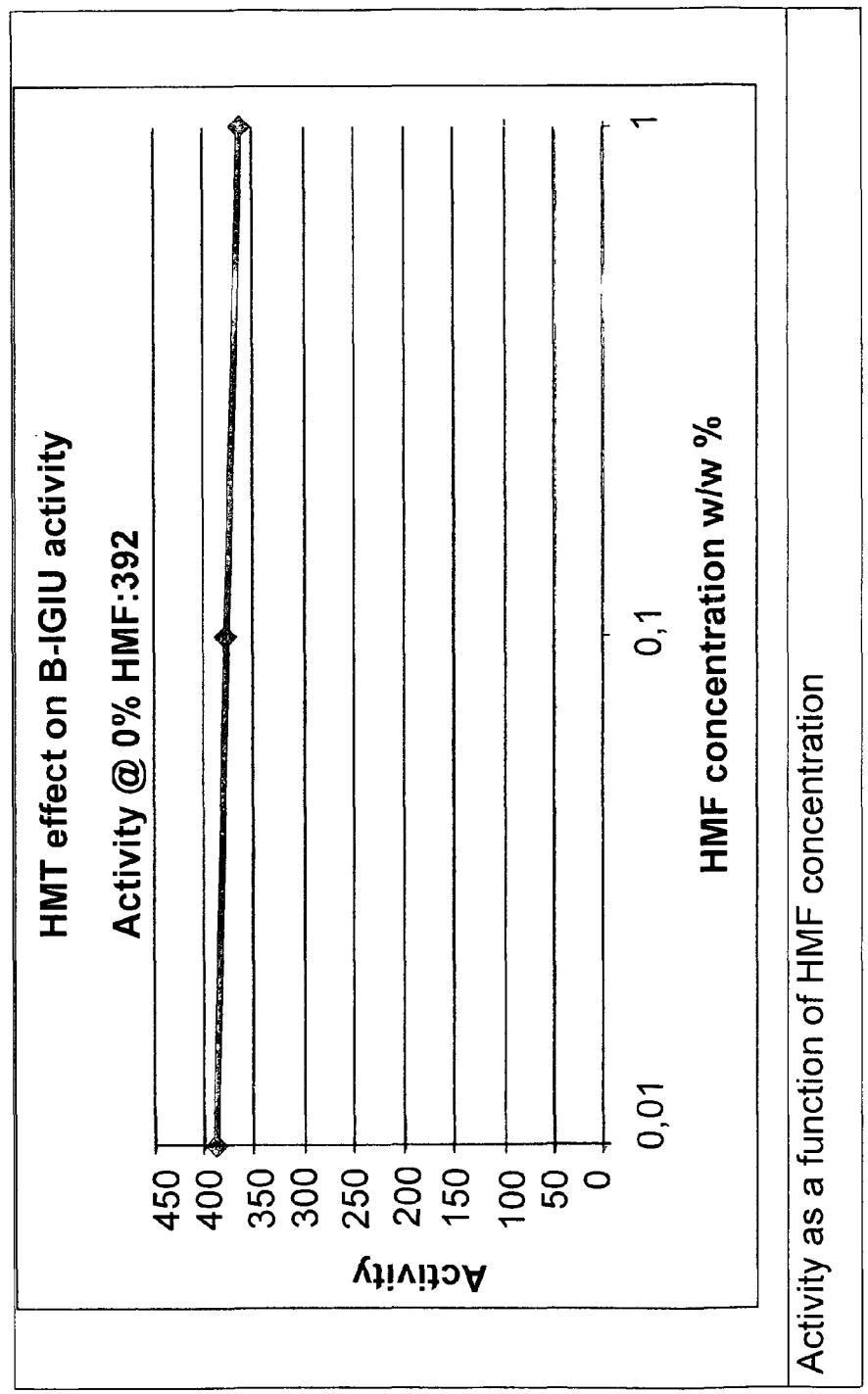
FIG. 13 shows the activity of glucose isomerase (Sweetzyme™) as a function of HMF concentration.

FIG. 13 shows the Sweetzyme™ activity as a function of HMF concentration and it can be seen that the activity is not seriously affected by the presence of HMF.

Example 14

Glucose Isomerase Performance with Substrate Containing NaCl and MIBK 3.44 gram immobilized glucose isomerase (Sweetzyme™) was loaded in a column heated to 60° C. and a substrate flow of 50 gram/hour was applied. The substrate was 45 w/w % sterile filtered glucose solution containing 1 g/L $MgSO_4.7H_2O$ and 0.18 g/L $NaS_2O_5$. To the substrate was added NaCl to a final concentration of 50 g/l and around 20 ml MIBK per liter glucose substrate which is enough to saturate the substrate with MIBK.

Samples were collected on a regular basis for HPLC analysis and the enzyme activity was calculated according to the following equation and the results are shown below in table 6 [Jorgensen, O. B., et al., Starch-Starke, 1988. 40(8), 307-313]:

$$A = 0.926 \frac{F_w}{w} X_e \frac{DP_1}{100} DS \ln \frac{X_e - X_i}{X_e - X}$$

where:
A: specific activity of immobilized enzyme (micromol/min/g enzyme) (IGIU/g: Immobilized Glucose Isomerase Units/g)
0.926: unit conversion factor
$F_w$: Flow rate of syrup (g/h)
w: Weight of enzyme (g)
$DP_1$: Inlet % of (glucose+fructose) in dry substance (100 at analytical conditions)
DS: Dry substance content (%)
X: Conversion=outlet % fructose/$DP_1$
Xi: inlet % fructose/$DP_1$
$X_e$: X at equilibrium (0.51 at 60° C.)
$DP_1$, $X_i$ and $X_e$ were assumed constant with following values:
$DP_1$: 99.7
$X_i$: 0
$X_e$: 0.5078

TABLE 6

Glucose isomerase activity as a function of time

| Time (h) | Activity (IGIU/g) | Substrate |
|---|---|---|
| 19.83 | 387.58 | Normal syrup |
| 93.58 | 395.15 | Normal syrup |
| 118.83 | 416.97 | Syrup with NaCl and MIBK |
| 140.75 | 433.99 | Syrup with NaCl and MIBK |
| 164.00 | 435.48 | Syrup with NaCl and MIBK |
| 187.33 | 437.58 | Syrup with NaCl and MIBK |
| 283.75 | 364.90 | Syrup with NaCl and MIBK |
| 308.25 | 378.56 | Syrup with NaCl and MIBK |
| 335.67 | 376.48 | Syrup with NaCl and MIBK |

After 9 days with the substrate containing NaCl and MIBK, the decay rate is not affected compared to a column with normal syrup.

Example 15

Glucose Isomerase Performance with Substrate Containing Hydroxymethylfurfural (HMF)

3.11 gram immobilized glucose isomerase (Sweetzyme™) was loaded in a column heated to 60° C. and a substrate flow of 50 gram/hour was applied. The substrate was 45 w/w % sterile filtered glucose solution containing 1 g/L $MgSO_4 \cdot 7H_2O$ and 0.18 g/L $NaS_2O_5$. To the substrate was added hydroxymethylfurfural (HMF) to a final concentration of 0.1 w/w % HMF.

Samples were collected on a regular basis for HPLC analysis and the enzyme activity was calculated according to the following equation and the results are shown below in table 7 [Jorgensen, O. B., et al., Starch-Starke, 1988. 40(8), 307-313]:

$$A = 0.926 \frac{F_w}{w} X_e \frac{DP_1}{100} DS \ln \frac{X_e - X_i}{X_e - X}$$

where:
A: specific activity of immobilized enzyme (micromol/min/g enzyme) (IGIU/g: Immobilized Glucose Isomerase Units/g)
0.926: unit conversion factor
$F_w$: Flow rate of syrup (g/h)
w: Weight of enzyme (g)
$DP_1$: Inlet % of (glucose+fructose) in dry substance (100 at analytical conditions)
DS: Dry substance content (%)
X: Conversion=outlet % fructose/$DP_1$
$X_i$: inlet % fructose/$DP_1$
$X_e$: X at equilibrium (0.51 at 60° C.)
$DP_1$, $X_i$ and $X_e$ were assumed constant with following values:
$DP_1$: 99.7
$X_i$: 0
$X_e$: 0.5078

TABLE 7

Glucose isomerase activity as a function of time

| Time (h) | Activity (IGIU/g) | Substrate |
|---|---|---|
| 68.50 | 376.93 | Normal syrup |
| 94.25 | 360.39 | Syrup with 0.1 w/w % HMF |
| 116.25 | 267.97 | Syrup with 0.1 w/w % HMF |
| 139.50 | 368.20 | Syrup with 0.1 w/w % HMF |
| 162.75 | 359.92 | Syrup with 0.1 w/w % HMF |
| 237.25 | 367.23 | Syrup with 0.1 w/w % HMF |
| 259.17 | 353.51 | Syrup with 0.1 w/w % HMF |
| 283.67 | 363.92 | Syrup with 0.1 w/w % HMF |
| 311.08 | 358.90 | Syrup with 0.1 w/w % HMF |

After 9 days with the substrate containing HMF, the decay rate is not affected compared to a column with normal syrup.

Example 16

Using a Combination of NaCl and Boric Acid as Catalysator

An aqueous solution containing 30 wt % fructose (3 mL, 5.7 mmol) was mounted in an Ace vial pressure tube (stable to ~20 Bar) and solid $B(OH)_3$ (0.3 g, 5 mmol) and/or solid NaCl (0.15 g, 3 mmol) were added to the solution. MIBK was added as extraction solvent so that an organic:aqueous volume ratio of 4:1 was obtained. The tube with the reaction mixture was placed in a preheated oil bath for a specified time under magnetic stirring (420 rpm) at a 150° C. (reaction times were measured after a stable oil bath temperature had been reached). After the reaction, the tube was removed from the oil bath and cooled to room temperature before a sample was taken for analysis. A sample of the reaction mixture was collected and filtered through a syringe filter (0.45 µm PTFE), mixed with an internal standard (i-PrOH) and analyzed via HPLC.

The results are shown below in Table 8.

TABLE 8

Dehydration of fructose to HMF with salt and/or boric acid in the aqueous phase

| Catalyst | HMF yield (%) | Fructose conversion (%) |
|---|---|---|
| None | 2 | 3 |
| 50 g/L NaCl | 5 | 13 |
| 100 g/L $B(OH)_3$ | 22 | 39 |
| 50 g/L NaCl and 100 g/L $B(OH)_3$ | 55 | 83 |

Example 17

The Effect of Different Salts Together with Boric Acid

An experiment similar to that described in example 16 was carried out using different salts in combination with boric acid.

An aqueous solution containing 30 wt % fructose (3 mL, 5.7 mmol) was mounted in an Ace vial pressure tube (stable to ~20 Bar) and solid $B(OH)_3$ (0.3 g, 5 mmol) and solid salt (3 mmol with respect to the anion) were added to the solution. MIBK was added as extraction solvent so that an organic:aqueous volume ratio of 4:1 was obtained. The tube with the reaction mixture was placed in a preheated oil bath for a specified time under magnetic stirring (420 rpm) at a 150° C. for 45 min (reaction times were measured after a stable oil bath temperature had been reached). After the reaction, the tube was removed from the oil bath and cooled to room temperature before a sample was taken for analysis. A sample of the reaction mixture was collected and filtered through a syringe filter (0.45 μm PTFE), mixed with an internal standard (i-PrOH) and analyzed via HPLC.

The results are shown below in table 9.

The R value indicated in table 9 is the HMF distribution obtained between the MIBK phase and the aqueous phase, i.e. $[HMF]_{MIBK}/[HMF]_{aq}$

TABLE 9

Dehydration of fructose to HMF with different salts and boric acid in the aqueous phase

| Salt | Fructose conversion (%) | HMF yield (%) | HMF selectivity (%) | R value (MIBK:aq) |
|---|---|---|---|---|
| LiCl | 69 | 45 | 66 | 1.1 |
| LiBr | 61 | 38 | 62 | 1.0 |
| LiNO$_3$ | 49 | 21 | 42 | 0.9 |
| NaCl | 70 | 46 | 65 | 1.0 |
| NaBr | 60 | 38 | 64 | 0.9 |
| NaNO$_3$ | 49 | 20 | 41 | 0.9 |
| Na$_2$SO$_4$ | 90 | 41 | 45 | 1.7 |
| KCl | 67 | 44 | 65 | 1.0 |
| KBr | 63 | 39 | 62 | 0.9 |
| KI | 56 | 35 | 63 | 0.7 |
| KNO$_3$ | 49 | 20 | 40 | 0.8 |
| K$_2$SO$_4$ | 89 | 40 | 46 | 1.5 |
| MgCl | 81 | 52 | 65 | 1.1 |
| AlCl$_3$ | 100 | 21 | 21 | 1.1 |
| FeCl$_3$ | 99 | 36 | 36 | 1.1 |

Example 18

Salt and Boric Acid as Catalysts with Different Organic Extraction Solvents

An experiment similar to that described in example 16 was carried out with different organic extraction solvents.

An aqueous solution containing 30 wt % fructose (3 mL, 5.7 mmol) was mounted in an Ace vial pressure tube (stable to ~20 Bar) and solid $B(OH)_3$ (0.3 g, 5 mmol) and NaCl (0.15 g, 3 mmol) were added to the solution. Different organic extraction solvent were added resulting in a organic:aqueous volume ratio of 4:1. The tube with the reaction mixture was placed in a preheated oil bath for a specified time under magnetic stirring (420 rpm) at a 150° C. (reaction times were measured after a stable oil bath temperature had been reached). After the reaction, the tube was removed from the oil bath and cooled to room temperature before a sample was taken for analysis. A sample of the reaction mixture was collected and filtered through a syringe filter (0.45 μm PTFE), mixed with an internal standard (i-PrOH) and analyzed via HPLC.

The results are shown below in table 10.

The R value indicated in table 10 is the HMF distribution obtained between the MIBK phase and the aqueous phase, i.e. $[HMF]_{MIBK}/[HMF]_{aq}$.

TABLE 10

Dehydration of fructose to HMF with different organic extraction solvents

| Organic extraction solvent | HMF yield (%) | Fructose conversion (%) | HMF selectivity (%) | R-value |
|---|---|---|---|---|
| MIBK | 46 | 70 | 65 | 1.0 |
| MIBK/2-BuOH; 7:3 | 50 | 72 | 70 | 1.9 |
| 2-BuOH | 37 | 59 | 63 | 2.3 |
| THF | 34 | 54 | 63 | 3.2 |
| THF/60 min | 38 | 63 | 60 | 3.7 |
| THF/75 min | 51 | 75 | 67 | 3.6 |

Example 19

Dehydration of Glucose and Sucrose to HMF with NaCl and Boric Acid as Catalyst An experiment similar to that described in example 16 was carried out with the exception that glucose and sucrose were used as substrates for dehydration to HMF.

An aqueous solution containing 30 wt % glucose (3 mL, 5.7 mmol) or sucrose (3 mL, 6.0 mmol) was mounted in an Ace vial pressure tube (stable to ~20 Bar) and solid $B(OH)_3$ (0.3 g, 5 mmol) and NaCl (0.15 g, 3 mmol) were added with the exception that some of the experiments with glucose as substrate no catalyst was included, i.e. no $B(OH)_3$ and NaCl. MIBK was added as organic extraction solvent in an amount resulting in a organic:aqueous volume ratio of 4:1. The tube with the reaction mixture was placed in a preheated oil bath for a specified time under magnetic stirring (420 rpm) at a 150° C. for the indicated periods of time (reaction times were measured after a stable oil bath temperature had been reached). After the reaction, the tube was removed from the oil bath and cooled to room temperature before a sample was taken for analysis. A sample of the reaction mixture was collected and filtered through a syringe filter (0.45 μm PTFE), mixed with an internal standard (i-PrOH) and analyzed via HPLC.

The results with glucose and sucrose as substrates are shown below in tables 11 and 12, respectively.

With sucrose as substrate (the data presented in Table 12) the calculated HMF selectivity is based on the assumption that all the produced HMF comes from conversion of the fructose in sucrose.

TABLE 11

Dehydration of glucose to HMF with NaCl and/or boric acid in the aqueous phase

| Catalyst | Time (min) | Glucose conversion (%) | HMF yield (%) | HMF selectivity (%) |
|---|---|---|---|---|
| None | 45 | | | |
| NaCl + B(OH)$_3$ | 45 | 8 | 2 | 25 |
| None | 180 | 13 | 1 | 10 |
| NaCl + B(OH)$_3$ | 180 | 36 | 10 | 27 |

TABLE 11-continued

Dehydration of glucose to HMF with NaCl and/or boric acid in the aqueous phase

| Catalyst | Time (min) | Glucose conversion (%) | HMF yield (%) | HMF selectivity (%) |
|---|---|---|---|---|
| None | 300 | 24 | 3 | 13 |
| NaCl + B(OH)$_3$ | 300 | 41 | 14 | 34 |

TABLE 12

Dehydration of sucrose to HMF with NaCl and/or boric acid in the aqueous phase

| Time (min) | Glucose yield (%) | Fructose yield (%) | HMF yield (%) | HMF selectivity (%) |
|---|---|---|---|---|
| 45 | 45 | 18 | 24 | 75 |
| 90 | 45 | 8 | 33 | 78 |
| 105 | 44 | 5 | 36 | 79 |
| 120 | 43 | 3 | 37 | 79 |

Example 20

Dehydration of Fructose to HMF with NaCl as Catalyst in a Continuous Reactor

Figure 14:
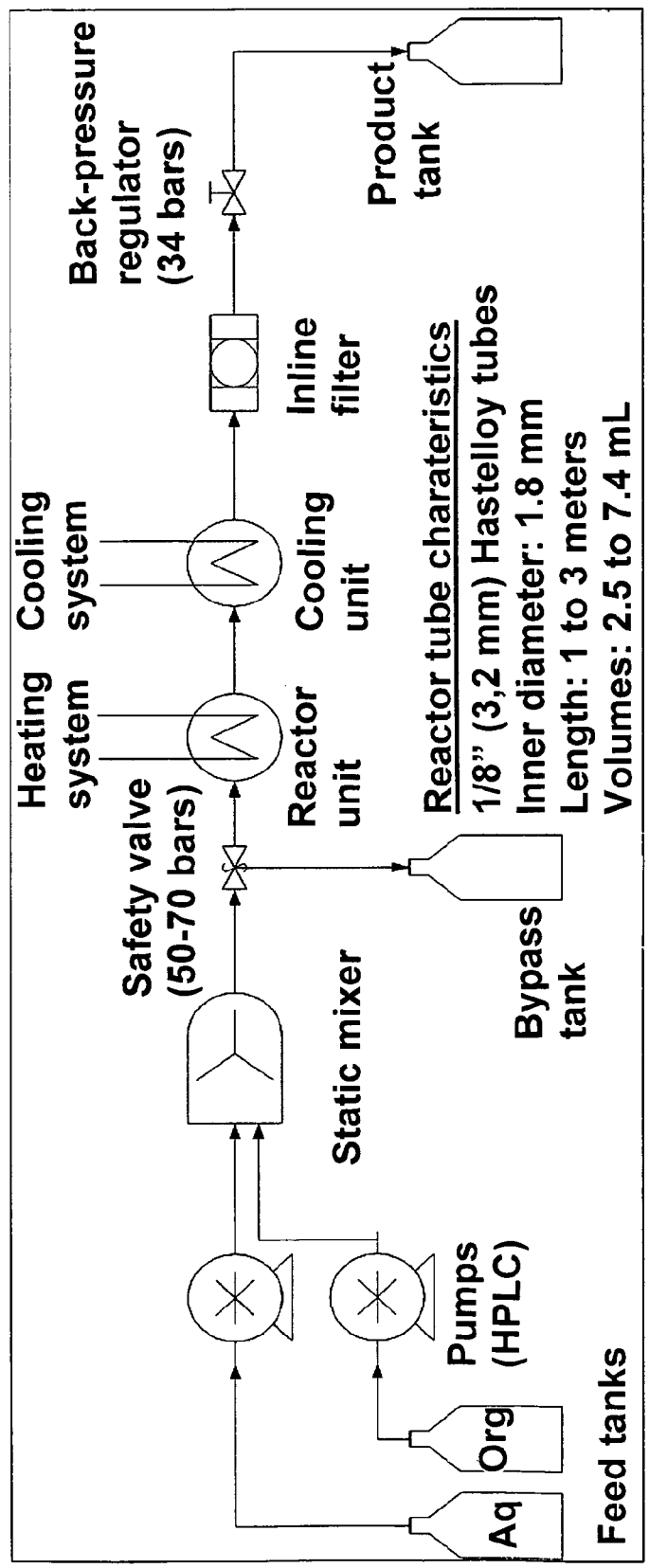
FIG. 14 shows the set-up of a laboratory scale mini-plant for continuous dehydration of glucose and fructose to HMF which was used in examples 20 and 21.

A laboratory scale mini-plant for continuous dehydration of glucose and fructose to HMF was built as shown in FIG. 14.

The reaction conditions are given in table 13. After the reaction the reaction mixture was cooled to room temperature before a sample was taken from the aqueous phase and filtered through a syringe filter (0.45 μm PTFE), and analyzed via HPLC.

Data for the fructose conversion, HMF yield, and HMF selectivity (HMF yield/fructose conversion) are also given in table 13.

The results show that a high yield and selectivity are maintained at high temperature (200° C.) and that high temperatures leads to reduced reaction times.

TABLE 13

Dehydration of fructose to HMF with NaCl as catalyst in a continuous reactor

| Temperature ° C. | Residence time (min) | Flow ml/min | Catalyst (w/w) | Substrate | Solvent (w:w) | Conv. Fructose | HMF yield | HMF Selectivity |
|---|---|---|---|---|---|---|---|---|
| 180 | 15 | 0.5 | 5% NaCl | 20% Fruc. | MIBK 4:1 | 98% | 71% | 72% |
| 180 | 15 | 0.5 | 5% NaCl | 20% Fruc. | MIBK 4:1 | 99% | 71% | 72% |
| 180 | 7.5 | 1.0 | 5% NaCl | 20% Fruc. | MIBK 4:1 | 87% | 64% | 74% |
| 180 | 7.5 | 1.0 | 5% NaCl | 20% Fruc. | MIBK 4:1 | 84% | 68% | 80% |
| 190 | 7.5 | 1.0 | 5% NaCl | 20% Fruc. | MIBK 4:1 | 98% | 74% | 76% |
| 200 | 3.75 | 0.66 | 5% NaCl | 20% Fruc. | MIBK 4:1 | 96% | 69% | 72% |
| 200 | 1.875 | 1.32 | 5% NaCl | 20% Fruc. | MIBK 4:1 | 87% | 60% | 70% |

Example 21

Dehydration of Fructose and Glucose Mixtures to HMF with NaCl as Catalyst in a Continuous Reactor The laboratory scale mini-plant in FIG. 14 was used for the experiments with the 5% NaCl and the solvent ratio of MIBK 4:1 also used in example 20.

Two substrates were used:

HFCS39 (61% glucose and 39% fructose) taken from the outlet of a laboratory column containing immobilized glucose isomerase (Sweetzyme) with inlet 100% glucose.

HFCS42 (58% glucose and 42% fructose) mixed from pure glucose and fructose substrates.

The substrate concentration was 300 g/L in all experiments.

The reaction conditions are given in table 14. After the reaction the product tank was cooled to room temperature before a sample was taken from the aqueous phase and filtered through a syringe filter (0.45 μm PTFE) and analyzed via HPLC.

Data for the fructose and glucose conversion, HMF yield, and HMF selectivity (HMF yield/(fructose+glucose conversion) are also given in table 14.

The results show that the selectivity is lower than for the pure fructose substrate in example 20. This is because the selectivity is calculated as the ratio of HMF and the total glucose and fructose conversion. If it was taken into account that most of the glucose is left unreacted then the selectivity would be similar to example 20.

The results show as in example 20 that a high yield is maintained at high temperature (200° C.) and that high temperatures leads to reduced reaction times.

TABLE 14

Dehydration of fructose and glucose mixtures to
HMF with NaCl as catalyst in a continuous reactor

| Temperature °C. | Residence time (min) | Flow (ml/min) | Substrate | Glucose (G) After reaction | Fructose (F) After reaction | Conv. G + F | HMF yield | HMF selectivity |
|---|---|---|---|---|---|---|---|---|
| 200 | 1.875 | 1.32 | HFCS42 | 43% | 7% | 49% | 25% | 51% |
| 200 | 1.875 | 1.32 | HFCS39 | 42% | 5% | 53% | 23% | 45% |
| 200 | 1.875 | 1.32 | HFCS39 | 43% | 8% | 49% | 22% | 45% |
| 200 | 3.75 | 0.66 | HFCS39 | 44% | 1% | 55% | 30% | 54% |
| 200 | 3.75 | 0.66 | HFCS42 | 43% | 6% | 52% | 26% | 51% |
| 180 | 7.5 | 0.33 | HFCS42 | 48% | 20% | 32% | 15% | 47% |
| 180 | 7.5 | 0.33 | HFCS42 | 48% | 20% | 32% | 15% | 48% |
| 190 | 7.5 | 0.33 | HFCS42 | 45% | 6% | 48% | 28% | 58% |

The invention claimed is:

1. A method of producing 5-hydroxymethylfurfural comprising subjecting a composition comprising fructose to a process in a reactor comprising a reaction medium, wherein said reaction medium comprises an aqueous phase and an organic phase and wherein said aqueous phase comprises a salt and has a pH in the range of 1.0 to 10, wherein the reaction medium does not comprise an acidic catalyst or does not comprise a strong acid.

2. The method of claim 1, which further comprises removing 5-hydroxymethylfurfural from the reactor.

3. The method of claim 1, wherein the composition comprising fructose also comprises glucose or mannose.

4. The method of claim 3, which further comprises prior to the subjecting step, subjecting the composition comprising glucose to an enzymatic reaction catalyzed by glucose isomerase, or subjecting the composition comprising mannose to an enzymatic reaction catalyzed by mannose isomerase.

5. The method of claim 3, which further comprises
  (a) Removing glucose or mannose from the reactor, and
  (b) Converting the glucose or mannose obtained to
    (i) 5-Hydroxymethylfurfural
    (ii) Fructose by an enzymatic reaction catalyzed by glucose isomerase or mannose isomerase.

6. The method of claim 1, wherein one or more of the steps are performed continuously.

7. The method of claim 1, wherein the concentration of salt in the aqueous phase of the reaction medium is in the range of 1-20 w/w %.

8. The method of claim 1, wherein the partition coefficient of the aqueous phase and the organic phase of the reaction medium with respect to 5-hydroxymethylfurfural is at least 1.0.

9. A method of producing 5-hydroxymethylfurfural comprising subjecting a composition comprising fructose to a process in a reactor comprising a reaction medium, wherein said reaction medium comprises an aqueous phase and an organic phase and wherein said aqueous phase comprises a salt, and wherein the reaction medium does not comprise an acidic catalyst or does not comprise a strong acid.

10. A method of producing 5-hydroxymethylfurfural comprising
  (a) subjecting a composition comprising glucose to an enzymatic reaction catalyzed by glucose isomerase, or subjecting a composition comprising mannose to an enzymatic reaction catalyzed by mannose isomerase,
  (b) subjecting a composition comprising fructose to a process in a reactor comprising a reaction medium, wherein said reaction medium comprises an aqueous phase and an organic phase and wherein said aqueous phase comprises a salt, wherein the reaction medium does not comprise an acidic catalyst or does not comprise a strong acid.

* * * * *